US011866512B2

(12) United States Patent
Holmdahl et al.

(10) Patent No.: US 11,866,512 B2
(45) Date of Patent: Jan. 9, 2024

(54) ANTIBODIES TO CITRULLINATED PROTEINS

(71) Applicant: VACARA AB, Solna (SE)

(72) Inventors: Rikard Holmdahl, Stockholm (SE);
Theo Rispens, EB Utrecht (NL);
Bingze Xu, Uppsala (SE); Changrong Ge, Sundbyberg (SE)

(73) Assignee: Vacara AB, Solna (SE)

( * ) Notice: Subject to any disclaimer, the term of this patent is extended or adjusted under 35 U.S.C. 154(b) by 0 days.

(21) Appl. No.: 16/765,752

(22) PCT Filed: Nov. 22, 2018

(86) PCT No.: PCT/EP2018/082236
§ 371 (c)(1),
(2) Date: May 20, 2020

(87) PCT Pub. No.: WO2019/101863
PCT Pub. Date: May 31, 2019

(65) Prior Publication Data
US 2020/0291133 A1   Sep. 17, 2020

(30) Foreign Application Priority Data

Nov. 22, 2017   (SE) .................................... 1730323-1

(51) Int. Cl.
C07K 16/36   (2006.01)
(52) U.S. Cl.
CPC .......... *C07K 16/36* (2013.01); *C07K 2317/24* (2013.01); *C07K 2317/33* (2013.01); *C07K 2317/41* (2013.01); *C07K 2317/52* (2013.01); *C07K 2317/55* (2013.01); *C07K 2317/565* (2013.01)

(58) Field of Classification Search
None
See application file for complete search history.

(56) References Cited

U.S. PATENT DOCUMENTS

| 6,180,370 | B1 * | 1/2001 | Queen ...................... A61P 31/12 |
| | | | 435/69.6 |
| 2017/0052179 | A1 * | 2/2017 | Salden ................... G01N 33/80 |

FOREIGN PATENT DOCUMENTS

| EP | 2332987 A1 | 6/2011 | | |
| WO | 2009/147201 A2 | 12/2009 | | |
| WO | WO-2011070172 A1 * | 6/2011 | .............. | A61P 17/06 |
| WO | 2013/109185 A1 | 7/2013 | | |
| WO | 2015/010791 A2 | 1/2015 | | |
| WO | 2017/139577 A1 | 8/2017 | | |

OTHER PUBLICATIONS

Jeffries, Roy. Nature reviews Drug discovery 8.3 (2009): 226-234 (Year: 2009).*
Janeway, Charles A. "Immunobiology: The Immune System in Health and Disease." 2005 (Year: 2005).*
Stryer, Biochemistry 4th, WH Freeman, New York. 1995 (Year: 1995).*
Colman, Research in Immunology 145.1 (1994): 33-36 (Year: 1994).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60. (Year: 2004).*
Aletaha, Daniel et al, Rheumatoid arthritis classification criteria, Arthritis Rheum, 62(9), 2569-2581, Year: 2010.
Allan, Rhys S. et al, Migratory dendritic cells transfer antigen to a lymph node-resident dendritic cell population for efficient CTL priming, Immunity, 25(1), 153-162, Jan. 7, 2006.
Amara, Khaled et al, Monoclonal IgG antibodies generated from joint-derived B cells of RA patients have a strong bias toward citrullinated autoantigen recognition, J Exp Med, 210(3), 445-55, Year 2013.
Amara, Khaled et al, Retraction: Monoclonal IgG antibodies generated from joint-derived B cells of RA patients have a strong bias toward citrullinated autoantigen recognition, J Exp Med, 216(1), 245-245, Year 2019.
Arnett, Frank C. et al, The American Rheumatism Association 1987 revised criteria for the classification of rheumatoid arthritis, Arthritis Rheum, 31(3), 315-24, Year 1988.
Ayoglu, Burcu et al, Autoantibody profiling in multiple sclerosis using arrays of human protein fragments, Mol Cell Proteomics, 12(9), 2657-72, Year 2013.
Burska, Agata N et al, Autoantibodies to Posttranslational Modifications in Rheumatoid Arthritis. Mediat Inflamm, 492873, Year 2014.
Chirivi, Renato G.S. et al, Anti-Citrullinated Protein Antibodies as Novel Therapeutic Drugs in Rheumatoid Arthritis, J Clin Cell Immunol, S6:006, Year 2013.
England, Bryant R. et al, Anticitrullinated protein antibodies: origin and role in the pathogenesis of rheumatoid arthritis, Curr Opin Rheumatol, 29(1), 57-64, Year 2017.
Ge, Changrong et al, Anti-citrullinated protein antibodies cause arthritis by cross-reactivity to joint cartilage, JCI Insight, 2(13), e93688, Year 2017.
Ge, Changrong et al, Structural basis of cross-reactivity of anti-citrullinated protein antibodies, Arthritis Rheumatol, 71(2), 210-221, Year 2018.
Ge, Changrong et al, Supplementary Data: Structural basis of cross-reactivity of anti-citrullinated protein antibodies, Arthritis Rheumatol, 71(2), 210-221, Year 2018.
Harre, Ulrike et al, Glycosylation of immunoglobulin G determines osteoclast differentiation and bone loss, Nat Commun, 6, 6651, Year 2015.
Harre, Ulrike et al, Induction of osteoclastogenesis and bone loss by human autoantibodies against citrullinated vimentin, J Clin Invest, 122(5), 1791-1802, Year 2012.

(Continued)

*Primary Examiner* — Michael Szperka
*Assistant Examiner* — Lia E Taylor
(74) *Attorney, Agent, or Firm* — Dinsmore & Shohl LLP

(57) ABSTRACT

The present disclosure concerns antibodies and antibody fragments binding to citrullinated proteins (ACPA), and their use in prevention and treatment of autoimmune diseases, specifically rheumatoid arthritis (RA).

14 Claims, 19 Drawing Sheets

Specification includes a Sequence Listing.

(56) References Cited

OTHER PUBLICATIONS

Haag, Sabrina et al, Identification of New Citrulline-Specific Autoantibodies, Which Bind to Human Arthritic Cartilage, by Mass Spectrometric Analysis of Citrullinated Type II Collagen, Arthritis Rheumatol, 66(6), 1440-1449, Year 2014.

Ioan-Facsinay, Andreea et al, Anti-cyclic citrullinated peptide antibodies are a collection of anti-citrullinated protein antibodies and contain overlapping and non-overlapping reactivities, Ann Rheum Dis, 70(1), 188-193, Year 2010.

Khmaladze, Ia et al, Mannan induces ROS-regulated, IL-17A-dependent psoriasis arthritis-like disease in mice, Proc Natl Acad Sci USA, 111(35), E3669-78, Year 2014.

Krishnamuthy Akilan et al, Identification of a novel chemokine-dependent molecular mechanism underlying rheumatoid arthritis-associated autoantibody-mediated bone loss, Ann Rheum Dis, 75(4):721-9, Year 2015.

McInnes, Iain B. et al, The pathogenesis of rheumatoid arthritis. N Engl J Med, 365 (23), 2205-2219, Year 2011.

Nandakumar, Kutty S. et al, Collagen type II (CII)-specific antibodies induce arthritis in the absence of T or B cells but the arthritis progression is enhanced by CII-reactive T cells, Arthritis Res Ther, 6(6), R544-5, Year 2004.

Nandakumar, Kutty S. et al, Collagen type II-specific monoclonal antibody-induced arthritis in mice: description of the disease and the influence of age, sex, and genes, Am J Pathol, 163(5), 1827-37, Year 2003.

Ohmi, Yuhsuke et al, Sialylation converts arthritogenic IgG into inhibitors of collagen-induced arthritis, Nat Commun, 7, 11205, Year 2016.

Rombouts, Yoann et al, Extensive glycosylation of ACPA-IgG variable domains modulates binding to citrullinated antigens in rheumatoid arthritis, Ann Rheum Dis, 75(3), 578-585, Year 2015.

Rombouts, Yoann et al, Anti-citrullinated protein antibodies acquire a pro-inflammatory Fc glycosylation phenotype prior to the onset of rheumatoid arthritis, Ann Rheum Dis, 74(1), 234-241, Year 2013.

Raats Jos M. et al, Recombinant human monoclonal autoantibodies specific for citrulline-containing peptides from phage display libraries derived from patients with rheumatoid arthritis, J Rheumatol, 30(8), 1696-711, Year 2003.

Schauer, Christine et al, Aggregated neutrophil extracellular traps limit inflammation by degrading cytokines and chemokines, Nat Med, 20(5), 511-7, Year 2014.

Schellekens, Gerard A. et al, The diagnostic properties of rheumatoid arthritis antibodies recognizing a cyclic citrullinated peptide. Arthritis Rheum, 43 (1), 155-163, Year 2000.

Steiner, Günter et al, Autoantibodies in rheumatoid arthritis and their clinical significance, Arthritis Res, 4 Suppl2 S1-S5, Year 2002.

Stolt, P et al, Quantification of the influence of cigarette smoking on rheumatoid arthritis: results from a population based case-control study, using incident cases, Ann Rheum Dis, 62(9), 835-41, Year 2003.

Svard, Anna et al, Associations with smoking and shared epitope differ between IgA- and IgG-class antibodies to cyclic citrullinated peptides in early rheumatoid arthritis, Arthritis Rheumatol, 67(8), 2032-7, Year 2015.

Trier, Nicole H et al, Contribution of Peptide Backbone to Anti-Citrullinated Peptide Antibody Reactivity, PLoS One, 10(12), e0144707, Year 2015.

Trier, Nicole H. et al Cross-reactivity of a human IgG(1) anticitrullinated fibrinogen monoclonal antibody to a citrullinated profilaggrin peptide, Protein Sci, 21(12), 1929-1941, Year 2012.

Trouw, L.A. et al, Anti-Cyclic Citrullinated Peptide Antibodies From Rheumatoid Arthritis Patients Activate Complement via Both the Classical and Alternative Pathways, Arthritis and Rheumatism, 60(7), 1923-1931, Year 2009.

Uysal, Huseyin et al, Structure and pathogenicity of antibodies specific for citrullinated collagen type II in experimental arthritis, J Exp Med, 206(2), 449-462, Year 2009.

Van De Stadt, Lotta A. et al, The extent of the anti-citrullinated protein antibody repertoire is associated with arthritis development in patients with seropositive arthralgia, Ann Rheum Dis, 70(1), 128-33, Year 2010.

Van De Stadt, Lotte A. et al, Monoclonal anti-citrullinated protein antibodies selected on citrullinated fibrinogen have distinct targets with different cross-reactivity patterns, Rheumatology (Oxford), 52(4), 631-635, Year 2012.

Van Gaalen, F.A. et al, Autoantibodies to cyclic citrullinated peptides predict progression to rheumatoid arthritis in patients with undifferentiated arthritis: a prospective cohort study. Arthritis Rheum, 50(3), 709-715, Year 2004.

Wigerblad, Gustaf et al, Autoantibodies to citrullinated proteins induce joint pain independent of inflammation via a chemokine-dependent mechanism, Ann Rheum Dis, 75(4), 730-738, Year 2015.

Winter, Graeme et al., Decision making in xia2, Acta Crystallogr D Biol Crystallogr, 69(Pt 7):1260-73, Year 2013.

Waaler, Erik et al, On the occurrence of a factor in human serum activating the specific agglutination of sheep blood corpuscles, APMIS, 17, 172-188, Year 1940.

* cited by examiner

A

B

E

F

A

B

C

D

E

F

G

A

B

Day of Observation

EIRA cohort (575 RA)

TIRA2 cohort (504 RA)

SEQUENCE LISTING

```
<160> NUMBER OF SEQ ID NOS: 24

<210> SEQ ID NO 1
<211> LENGTH: 7
<212> TYPE: PRT
<213> ORGANISM: Homo sapiens

<400> SEQUENCE: 1

Ser Glu Ser Tyr Phe Trp Gly
1               5

<210> SEQ ID NO 2
<211> LENGTH: 7
<212> TYPE: PRT
```

```
<213> ORGANISM: Homo sapiens

<400> SEQUENCE: 2

Asn Glu Ser Tyr Phe Trp Gly
1               5

<210> SEQ ID NO 3
<211> LENGTH: 9
<212> TYPE: PRT
<213> ORGANISM: Homo sapiens

<400> SEQUENCE: 3

Ser Val Ile His Thr Gly Thr Thr Tyr
1               5

<210> SEQ ID NO 4
<211> LENGTH: 9
<212> TYPE: PRT
<213> ORGANISM: Homo sapiens

<400> SEQUENCE: 4

Ile Arg Gly Gly Ser Ser Asn Trp Leu
1               5

<210> SEQ ID NO 5
<211> LENGTH: 8
<212> TYPE: PRT
<213> ORGANISM: Homo sapiens

<400> SEQUENCE: 5

Asp Ser Ile Leu Arg Ser Ala Phe
1               5

<210> SEQ ID NO 6
<211> LENGTH: 6
<212> TYPE: PRT
<213> ORGANISM: Homo sapiens

<400> SEQUENCE: 6

Asp Asp Arg Gln Arg Pro
1               5

<210> SEQ ID NO 7
<211> LENGTH: 8
<212> TYPE: PRT
<213> ORGANISM: Homo sapiens

<400> SEQUENCE: 7

Trp Asn Gly Arg Leu Ser Ala Phe
1               5

<210> SEQ ID NO 8
<211> LENGTH: 120
<212> TYPE: PRT
<213> ORGANISM: Homo sapiens

<400> SEQUENCE: 8

Gln Val Gln Leu Glu Glu Ser Gly Pro Gly Leu Val Arg Pro Ser Glu
1               5                   10                  15

Thr Leu Ser Leu Ser Cys Thr Val Ser Gly Phe Pro Met Ser Glu Ser
            20                  25                  30

Tyr Phe Trp Gly Trp Ile Arg Gln Ser Pro Gly Lys Gly Leu Glu Trp
        35                  40                  45
```

Leu Gly Ser Val Ile His Thr Gly Thr Thr Tyr Tyr Arg Pro Ser Leu
 50                  55                  60

Glu Ser Arg Leu Thr Ile Ala Met Asp Pro Ser Lys Asn Gln Val Ser
 65                  70                  75                  80

Leu Ser Leu Thr Ser Val Thr Val Ala Asp Ser Ala Met Tyr Tyr Cys
                 85                  90                  95

Val Arg Ser Val Ile His Thr Gly Thr Thr Tyr Asp Pro Trp Gly Pro
                100                 105                 110

Gly Ile Val Val Thr Val Ser Ser
            115                 120

<210> SEQ ID NO 9
<211> LENGTH: 120
<212> TYPE: PRT
<213> ORGANISM: Homo sapiens

<400> SEQUENCE: 9

Gln Val Gln Leu Glu Glu Ser Gly Pro Gly Leu Val Arg Pro Ser Glu
 1               5                  10                  15

Thr Leu Ser Leu Ser Cys Thr Val Ser Gly Phe Pro Met Asn Glu Ser
                 20                  25                  30

Tyr Phe Trp Gly Trp Ile Arg Gln Ser Pro Gly Lys Gly Leu Glu Trp
             35                  40                  45

Leu Gly Ser Val Ile His Thr Gly Thr Thr Tyr Tyr Arg Pro Ser Leu
 50                  55                  60

Glu Ser Arg Leu Thr Ile Ala Met Asp Pro Ser Lys Asn Gln Val Ser
 65                  70                  75                  80

Leu Ser Leu Thr Ser Val Thr Val Ala Asp Ser Ala Met Tyr Tyr Cys
                 85                  90                  95

Val Arg Ser Val Ile His Thr Gly Thr Thr Tyr Asp Pro Trp Gly Pro
                100                 105                 110

Gly Ile Val Val Thr Val Ser Ser
            115                 120

<210> SEQ ID NO 10
<211> LENGTH: 120
<212> TYPE: PRT
<213> ORGANISM: Homo sapiens

<400> SEQUENCE: 10

Gln Val Gln Leu Glu Glu Ser Gly Pro Gly Leu Val Arg Pro Ser Glu
 1               5                  10                  15

Thr Leu Ser Leu Ser Cys Thr Val Ser Gly Phe Pro Met Ser Glu Ser
                 20                  25                  30

Tyr Phe Trp Gly Trp Ile Arg Gln Ser Pro Gly Lys Gly Leu Glu Trp
             35                  40                  45

Leu Gly Ser Val Ile His Thr Gly Thr Thr Tyr Tyr Arg Pro Ser Leu
 50                  55                  60

Glu Ser Arg Leu Thr Ile Ala Met Asp Pro Ser Lys Asn Gln Val Ser
 65                  70                  75                  80

Leu Ser Leu Thr Ser Val Thr Val Ala Asp Ser Ala Met Tyr Tyr Cys
                 85                  90                  95

Val Arg Ser Val Ile His Thr Gly Thr Thr Tyr Asp Pro Trp Gly Pro
                100                 105                 110

Gly Ile Val Val Thr Ala Ser Ser
            115                 120

```
<210> SEQ ID NO 11
<211> LENGTH: 120
<212> TYPE: PRT
<213> ORGANISM: Homo sapiens

<400> SEQUENCE: 11

Gln Val Gln Leu Glu Glu Ser Gly Pro Gly Leu Val Arg Pro Ser Glu
1               5                   10                  15

Thr Leu Ser Leu Ser Cys Thr Val Ser Gly Phe Pro Met Asn Glu Ser
            20                  25                  30

Tyr Phe Trp Gly Trp Ile Arg Gln Ser Pro Gly Lys Gly Leu Glu Trp
        35                  40                  45

Leu Gly Ser Val Ile His Thr Gly Thr Thr Tyr Tyr Arg Pro Ser Leu
    50                  55                  60

Glu Ser Arg Leu Thr Ile Ala Met Asp Pro Ser Lys Asn Gln Val Ser
65                  70                  75                  80

Leu Ser Leu Thr Ser Val Thr Val Ala Asp Ser Ala Met Tyr Tyr Cys
                85                  90                  95

Val Arg Ser Val Ile His Thr Gly Thr Thr Tyr Asp Pro Trp Gly Pro
            100                 105                 110

Gly Ile Val Val Thr Ala Ser Ser
        115                 120

<210> SEQ ID NO 12
<211> LENGTH: 112
<212> TYPE: PRT
<213> ORGANISM: Homo sapiens

<400> SEQUENCE: 12

Gln Ser Val Trp Thr Gln Pro Pro Ser Val Ser Ala Ala Pro Gly Gln
1               5                   10                  15

Lys Val Thr Ile Ser Cys Ser Gly Asp Asp Ser Ile Leu Arg Ser Ala
            20                  25                  30

Phe Val Ser Trp Tyr Gln Gln Val Pro Gly Ser Ala Pro Lys Leu Val
        35                  40                  45

Ile Phe Asp Asp Arg Gln Arg Pro Ser Gly Ile Pro Ala Arg Phe Ser
    50                  55                  60

Gly Ser Asn Ser Gly Thr Thr Ala Thr Leu Asp Ile Ala Gly Leu Gln
65                  70                  75                  80

Arg Gly Asp Glu Ala Asp Tyr Tyr Cys Ala Ala Trp Asn Gly Arg Leu
                85                  90                  95

Ser Ala Phe Val Phe Gly Ser Gly Thr Thr Val Ser Val Leu Arg Thr
            100                 105                 110

<210> SEQ ID NO 13
<211> LENGTH: 112
<212> TYPE: PRT
<213> ORGANISM: Homo sapiens

<400> SEQUENCE: 13

Gln Ser Val Trp Thr Gln Pro Pro Ser Val Ser Ala Ala Pro Gly Gln
1               5                   10                  15

Asn Val Thr Ile Ser Cys Ser Gly Asp Asp Ser Ile Leu Arg Ser Ala
            20                  25                  30

Phe Val Ser Trp Tyr Gln Gln Val Pro Gly Ser Ala Pro Lys Leu Val
        35                  40                  45

Ile Phe Asp Asp Arg Gln Arg Pro Ser Gly Ile Pro Ala Arg Phe Ser
```

```
            50                  55                  60
Gly Ser Asn Ser Gly Thr Thr Ala Thr Leu Asp Ile Ala Gly Leu Gln
 65                  70                  75                  80

Arg Gly Asp Glu Ala Asp Tyr Tyr Cys Ala Ala Trp Asn Gly Arg Leu
                 85                  90                  95

Ser Ala Phe Val Phe Gly Ser Gly Thr Thr Val Ser Val Leu Arg Thr
            100                 105                 110
```

<210> SEQ ID NO 14
<211> LENGTH: 111
<212> TYPE: PRT
<213> ORGANISM: Homo sapiens

<400> SEQUENCE: 14

```
Gln Ser Val Trp Thr Gln Pro Pro Ser Val Ser Ala Ala Pro Gly Gln
  1               5                  10                  15

Lys Val Thr Ile Ser Cys Ser Gly Asp Asp Ser Ile Leu Arg Ser Ala
             20                  25                  30

Phe Val Ser Trp Tyr Gln Gln Val Pro Gly Ser Ala Pro Lys Leu Val
         35                  40                  45

Ile Phe Asp Asp Arg Gln Arg Pro Ser Gly Ile Pro Ala Arg Phe Ser
     50                  55                  60

Gly Ser Asn Ser Gly Thr Thr Ala Thr Leu Asp Ile Ala Gly Leu Gln
 65                  70                  75                  80

Arg Gly Asp Glu Ala Asp Tyr Tyr Cys Ala Ala Trp Asn Gly Arg Leu
                 85                  90                  95

Ser Ala Phe Val Phe Gly Ser Gly Thr Lys Leu Thr Val Leu Gly
            100                 105                 110
```

<210> SEQ ID NO 15
<211> LENGTH: 111
<212> TYPE: PRT
<213> ORGANISM: Homo sapiens

<400> SEQUENCE: 15

```
Gln Ser Val Trp Thr Gln Pro Pro Ser Val Ser Ala Ala Pro Gly Gln
  1               5                  10                  15

Asn Val Thr Ile Ser Cys Ser Gly Asp Asp Ser Ile Leu Arg Ser Ala
             20                  25                  30

Phe Val Ser Trp Tyr Gln Gln Val Pro Gly Ser Ala Pro Lys Leu Val
         35                  40                  45

Ile Phe Asp Asp Arg Gln Arg Pro Ser Gly Ile Pro Ala Arg Phe Ser
     50                  55                  60

Gly Ser Asn Ser Gly Thr Thr Ala Thr Leu Asp Ile Ala Gly Leu Gln
 65                  70                  75                  80

Arg Gly Asp Glu Ala Asp Tyr Tyr Cys Ala Ala Trp Asn Gly Arg Leu
                 85                  90                  95

Ser Ala Phe Val Phe Gly Ser Gly Thr Lys Leu Thr Val Leu Gly
            100                 105                 110
```

<210> SEQ ID NO 16
<211> LENGTH: 330
<212> TYPE: PRT
<213> ORGANISM: Homo sapiens

<400> SEQUENCE: 16

```
Ala Ser Thr Lys Gly Pro Ser Val Phe Pro Leu Ala Pro Ser Ser Lys
  1               5                  10                  15
```

-continued

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 107
<212> TYPE: PRT
<213> ORGANISM: Homo sapiens

<400> SEQUENCE: 17

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser

```
                    50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 18
<211> LENGTH: 106
<212> TYPE: PRT
<213> ORGANISM: Homo sapiens

<400> SEQUENCE: 18

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 19
<211> LENGTH: 17
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Citrulline

<400> SEQUENCE: 19

Asn Glu Glu Gly Phe Phe Ser Ala Xaa Gly His Arg Pro Leu Asp Lys
 1               5                  10                  15

Lys

<210> SEQ ID NO 20
<211> LENGTH: 18
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Citrulline

<400> SEQUENCE: 20

Cys Pro Ala Gly Glu Glu Gly Lys Xaa Gly Ala Arg Gly Glu Pro Gly
 1               5                  10                  15

Cys Ala

<210> SEQ ID NO 21
<211> LENGTH: 18
<212> TYPE: PRT
<213> ORGANISM: Homo sapiens
```

```
<220> FEATURE:
<221> NAME/KEY: MISC_FEATURE
<222> LOCATION: (9)..(9)
<223> OTHER INFORMATION: Xaa is Citrulline

<400> SEQUENCE: 21

Cys Glu Ala Gly Glu Pro Gly Glu Xaa Gly Leu Lys Gly His Arg Gly
1               5                  10                  15

Cys Ala

<210> SEQ ID NO 22
<211> LENGTH: 20
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Citruline
<220> FEATURE:
<221> NAME/KEY: MISC_FEATURE
<222> LOCATION: (12)..(12)
<223> OTHER INFORMATION: Xaa is Citruline

<400> SEQUENCE: 22

Cys Lys Ile His Ala Xaa Glu Ile Phe Asp Ser Xaa Gly Asn Pro Thr
1               5                  10                  15

Val Glu Cys Lys
            20

<210> SEQ ID NO 23
<211> LENGTH: 120
<212> TYPE: PRT
<213> ORGANISM: Mus musculus

<400> SEQUENCE: 23

Gln Val Gln Leu Glu Glu Ser Gly Pro Gly Leu Val Arg Pro Ser Glu
1               5                  10                  15

Thr Leu Ser Leu Ser Cys Thr Val Ser Gly Phe Pro Met Ser Glu Ser
            20                  25                  30

Tyr Phe Trp Gly Trp Ile Arg Gln Ser Pro Gly Lys Gly Leu Glu Trp
        35                  40                  45

Leu Gly Ser Val Ile His Thr Gly Thr Thr Tyr Tyr Arg Pro Ser Leu
    50                  55                  60

Glu Ser Arg Leu Thr Ile Ala Met Asp Pro Ser Lys Asn Gln Val Ser
65                  70                  75                  80

Leu Ser Leu Thr Ser Val Thr Val Ala Asp Ser Ala Met Tyr Tyr Cys
                85                  90                  95

Val Arg Ile Arg Gly Gly Ser Ser Asn Trp Leu Asp Pro Trp Gly Pro
            100                 105                 110

Gly Ile Val Val Thr Ala Ser Ser
        115                 120

<210> SEQ ID NO 24
<211> LENGTH: 120
<212> TYPE: PRT
<213> ORGANISM: Homo sapiens

<400> SEQUENCE: 24

Gln Val Gln Leu Glu Glu Ser Gly Pro Gly Leu Val Arg Pro Ser Glu
1               5                  10                  15

Thr Leu Ser Leu Ser Cys Thr Val Ser Gly Phe Pro Met Ser Glu Ser
            20                  25                  30
```

```
Tyr Phe Trp Gly Trp Ile Arg Gln Ser Pro Gly Lys Gly Leu Glu Trp
        35                  40                  45

Leu Gly Ser Val Ile His Thr Gly Thr Thr Tyr Tyr Arg Pro Ser Leu
    50                  55                  60

Glu Ser Arg Leu Thr Ile Ala Met Asp Pro Ser Lys Asn Gln Val Ser
65              70                  75                      80

Leu Ser Leu Thr Ser Val Thr Val Ala Asp Ser Ala Met Tyr Tyr Cys
                85                  90                  95

Val Arg Ile Arg Gly Gly Ser Ser Asn Trp Leu Asp Pro Trp Gly Pro
            100                 105                 110

Gly Ile Val Val Thr Val Ser Ser
        115                 120
```

ANTIBODIES TO CITRULLINATED PROTEINS

CROSS REFERENCE TO RELATED APPLICATIONS

This application is a U.S. National Stage of international application PCT/EP2018/082236 filed Nov. 22, 2018, which claims priority to Swedish Application No: 1730323-1 filed Nov. 22, 2017, the entire contents of each of which are incorporated herein by reference.

FIELD OF THE INVENTION

The present invention relates to antibodies binding to citrullinated proteins (ACPA), and their use in the diagnosis, prevention, and treatment of autoimmune diseases, specifically rheumatoid arthritis (RA).

SEQUENCE LISTING

The present application includes a sequence listing entitled "VACA0001PA_SEQ.txt", created on Oct. 4, 2022 and have a size of 18,037 bytes.

BACKGROUND TO THE INVENTION

A common characteristic feature of autoimmune diseases is the production of the hallmark autoantibodies. The occurrence of rheumatoid factors (RF), antibodies self-reactive with the Fc portion of immunoglobulin G (IgG) representing the serological marker of rheumatoid arthritis (RA) (Waaler, E. 1939), was first described in RA patients almost a century ago. RF can be detected in 60-80% of RA patients but has a modest specificity since it is also present in patients with other autoimmune diseases (Steiner et al., 2002). More recently, another class of anti-citrullinated protein antibodies (ACPAs) has been found to be highly specific for RA and is suggested to be implicated in disease development (Schellekens et al., 2011). Both RF and ACPA appear years before the clinical onset of RA (McInnes et al., 2011).

Due to their diagnostic potentials, both RF and ACPA are now included in the ACR/EULAR classification criteria for RA. ACPAs are typically detected by commercial ELISA using a certain set of undisclosed (CCP2) citrullinated peptides. Particularly, up to 70% of RA patients are found to be CCP2 positive, and occurrence of these ACPAs is believed to be associated with more severe clinical outcomes (van Gaalen et al., 2004), thereby providing the possibility of an early appropriate intervention in RA.

A variety of autoantigens has been characterized to be potential targets of ACPAs such as α-enolase, fibrinogen, filaggrin, vimentin, and collagen type II (CII) upon citrullination (Burska et al., 2014). Some ACPAs may have a more specific reactivity to citrulline on certain proteins but most seem to be widely cross-reactive (Ge et al., 2017; Haag et al., 2014; Trier et al., 2015; Trier et al., 2012).

It is commonly believed that ACPAs are pathogenic and contribute to the development of arthritis. It has previously been described that ACPAs occur before arthritis, are associated with onset of arthritis and arthritis severity, induce bone erosion in animal models and activate human osteoclasts in vitro (Harre et al., 2012). The bone erosion has been suggested to be due to that ACPA specifically activate osteoclasts to secrete IL8. It has also been described that ACPAs activate inflammatory macrophages in vitro. Thus, ACPAs are capable to induce TNF-α secretion from macrophage through engagement with the Fc-receptor and mediate complement activation via both the classical and alternative pathways (Trouw et al., 2009). Furthermore, ACPAs are associated with bone erosion before onset of arthritis, induce behavioral associated pain in animal models (Wigerblad et al., 2016) and arthralgia, are developed before the onset of clinical arthritis and induce as well as enhance development of arthritis. However, these phenomenas have been questioned and despite extensive studies there is no established dogma on how they induce and enhance arthritis. It is believed that both RF and ACPA promote the formation of immune complexes, but their pathogenic role in vivo remains unclear. It is still unclear whether the reported bone erosion and osteoclast activating effects are specifically related to their citrulline specificity or to other intrinsic characteristics such as Fc glycosylation (Rombouts et al., 2015; Harre et al., 2015).

So far, only a subtype of ACPA cross-reactive with joint cartilage has been shown to be able to induce arthritis upon direct injection into mice (Ge et al., 2017; Uysal et al., 2009).

Most ACPA-positive sera from RA are however widely cross-reactive with many citrullinated peptides with limited influence of the peptide sequence (Ioan-Facsinay et al., 2011) and the molecular interactions governing the cross-reactivity and specificity of ACPA on a molecular level remain elusive. Furthermore, the biological effector functions of these citrulline-specific but cross-reactive ACPAs and whether they promote or protect against arthritis are largely unknown.

Two monoclonal ACPAs isolated from RA patients have previously been described (van de Stadt et al., 2013) and it was showed that the N-linked glycans in the variable domains could modulate their binding profiles to citrullinated antigens (Rombouts et al., 2016). These antibodies have been the first and so far the only antibodies classified as ACPA to be confirmed molecularly with crystallization analysis (Ge et al Arthritis Rheum 2018).

Some reported ACPAs (Amara et al., 2013) could not be confirmed by additional specificity studies (Ge et al., 2018) and are therefore to be regarded as antibodies with unknown specificity, disqualifying several previous studies based on their believed ACPA reactivity (Krishnamurthy et al., 2016).

SUMMARY

The present invention provides antibodies and antibody fragments that bind to citrullinated proteins (ACPA) and that surprisingly show therapeutic effect in rheumatoid arthritis.

In one aspect, the present invention provides an antibody or antibody fragment comprising a variable heavy chain (VH) domain and/or a variable light chain (VL) domain, and wherein
(a) the VH domain comprises an amino acid sequence that includes one, two or three complementarity determining regions (CDRs) selected from the group consisting of:
a CDR1 sequence comprising an amino acid sequence having at least 57%, 71%, 86%, or 100% sequence identity to the sequence of SEQ ID NO: 1 or 2;
a CDR2 sequence comprising an amino acid sequence having at least 56%, 67%, 78%, 89%, or 100% sequence identity to the sequence of SEQ ID NO: 3; and a CDR3 sequence comprising an amino acid sequence having at least 56%, 67%, 78%, 89%, or 100% sequence identity to the sequence of SEQ ID NO: 4 and/or
(b) the VL domain comprises an amino acid sequence that includes one, two or three complementarity determining regions (CDRs) selected from the group consisting of:
a CDR4 sequence comprising an amino acid sequence having at least 50%, 63%, 75%, 88%, or 100% sequence identity to the sequence of SEQ ID NO: 5;
a CDR5 sequence comprising an amino acid sequence having at least 50%, 67%, 83%, or 100% sequence identity to the sequence of SEQ ID NO: 6;
a CDR6 sequence comprising an amino acid sequence having at least 50%, 63%, 75%, 88%, or 100% sequence identity to the sequence of SEQ ID NO: 7.

In one aspect, the present invention provides a polynucleotide encoding an antibody or an antibody fragment according to the above aspect.

In one aspect, the present invention provides a vector comprising the polynucleotide of the above aspect.

In one aspect, the present invention provides a host cell comprising the polynucleotide, the antibody or the antibody fragment and/or the vector according to the above aspects.

In one aspect, the present invention provides a composition comprising the antibody or the antibody fragment, the polynucleotide, the vector and/or the cell according to any of the above aspects.

In one aspect, the present invention provides the antibody or the antibody fragment, the polynucleotide, the vector, the cell, and/or the composition according to any of the above aspects for use in medicine.

In one aspect, the present invention provides the antibody or the antibody fragment, the polynucleotide, the vector, the cell, and/or the composition according to any of the above aspects for use in the prevention, prophylaxis and/or treatment of an autoimmune disease or disorder.

In one aspect, the present invention provides the use of the antibody or the antibody fragment, the composition, the polynucleotide, the vector, the cell, and/or the composition according to any one of the above aspects for the manufacture of a medicament for the treatment of an autoimmune disease or disorder.

In one aspect, the present invention provides a method of preventing and/or treating an autoimmune disease or disorder, the method comprising administering the antibody or the antibody fragment, the polynucleotide, the vector, the cell, and/or the composition according to any one of the above aspects to a subject in need thereof.

In one aspect, the present invention provides a method of reducing the amount of pro-inflammatory immune cells and/or increasing the amount of anti-inflammatory immune cells, the method comprising administering a therapeutically effective amount of the antibody or the antibody fragment, the polynucleotide, the vector, the cell, and/or the composition according to any of the above aspects to a subject in need thereof.

In one aspect, the present invention provides an in vitro method comprising culturing cells in the presence of the antibody or the antibody fragment according to the above aspects.

In one aspect, the present invention provides a method of producing an antibody or an antibody fragment according to any of the above aspects comprising culturing a host cell according to the above aspect, and recovering therefrom an antibody or an antibody fragment according to any of the above aspects.

In one aspect, the present invention provides a method of preparing a variant of the antibody or antibody fragments according to any one of the above aspects, which variant retains the ability to bind to a citrullinated peptide, the method comprising—
(i) providing a polynucleotide according to the above aspects encoding a parent antibody or antibody fragment;
(ii) introducing one or more nucleotide mutations into the amino acid coding regions of the nucleic acid sequence, optionally within the regions encoding the VH and/or VL domain(s), such that the mutated nucleic acid encodes a variant antibody or antibody fragment having a different amino acid sequence compared to the parent antibody or antibody fragment;
(iii) expressing the variant antibody or antibody fragment that is encoded by the mutated nucleic acid sequence; and
(iv) comparing the ability of the variant antibody or antibody fragment and the parent antibody or antibody fragment to bind to a citrullinated peptide.

DESCRIPTION OF THE DRAWINGS

FIG. 1(A) The reactivity profiles (i.e., MFI) of each peptide against two variants (WT: glycosylated, NG: non-glycosylated) of E4 and F3 were analyzed in a Luminex immunoassay. A set of 108 cyclic 17-mer CII peptides (54 citrullinated and 54 corresponding non-modified ones) covering the whole mature CII with arginine or citrulline centered in the sequence was designed and used in the assay. In addition, some other citrullinated peptides were also included. The dashed line indicates the positivity threshold, defined as the mean plus 2xSD of MFI values obtained for the all 54 non-modified peptides.

FIG. 1(B) Reactivity of the corresponding non-modified arginine-containing peptides.

(D). Quantification of osteoclast number in cartilage sections (n=4-6 per group, the whole surface area lining both tibia and talus/mouse was evaluated).
i. chimeric E4NG(3 mg)+M2139(3 mg), ii. chimeric E4NG(3 mg)+M2139(6 mg),
iii. M2139(3 mg)+M2139mut(3 mg), iv. ACC1(3 mg)+M2139(3 mg),
v. ACC1(3 mg)+M2139(6 mg),
(E) Mean arthritis score in CIA9i mice. Data are presented as mean±SE and include both arthritic and healthy animals.
(F) CAIA incidence in CIA9i mice. Data represent CAIA assessment.
-○—ACC1(3 mg)+M2139(3 mg), -△—F3 (3 mg)+M2139(3 mg),
-■—M2139(3 mg)+M2139mut(3 mg), -●—E4(3 mg)+M2139(3 mg),
All graphs represent mean and standard deviation, n.s., no significance, *P<0.05, P<0.01, *P<0.001, ****P<0.0001, Mann-Whitney U-test.

Figure 3:
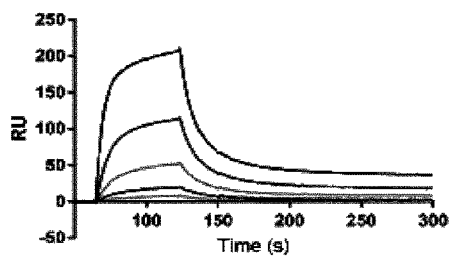
Figure 3:
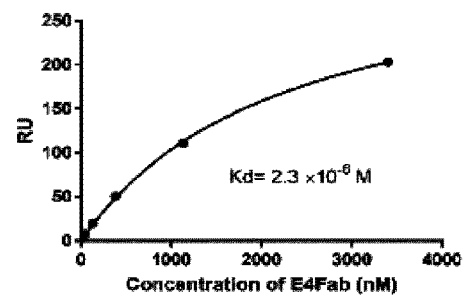
Figure 3:
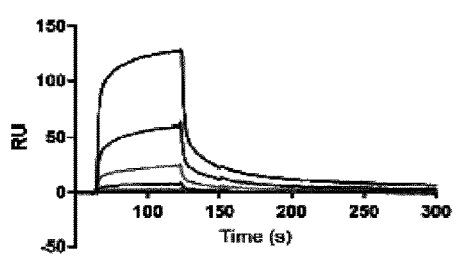
Figure 3:
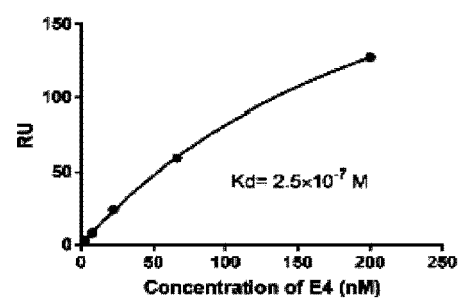
Figure 3:
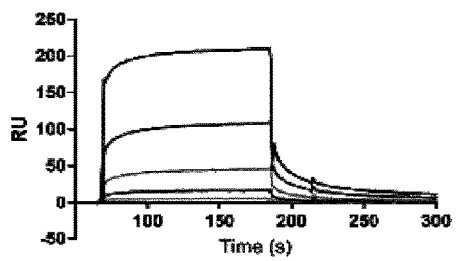
Figure 3:
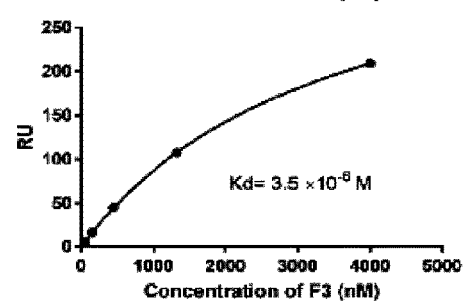
Figure 3:
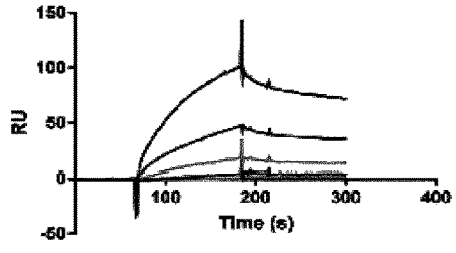
Figure 3:
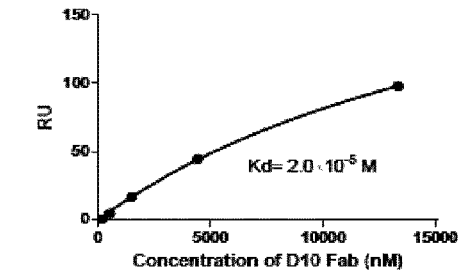
Figure 3:
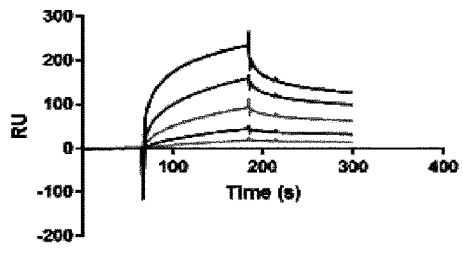
Figure 3:
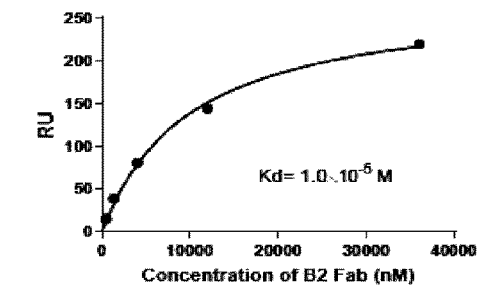
Figure 3:
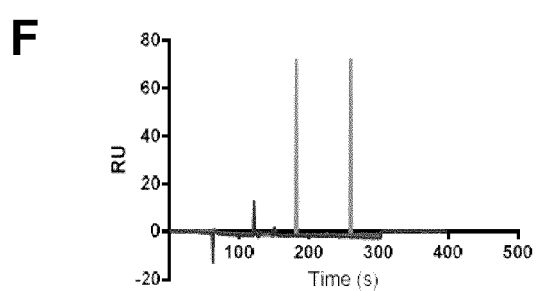
Figure 3:
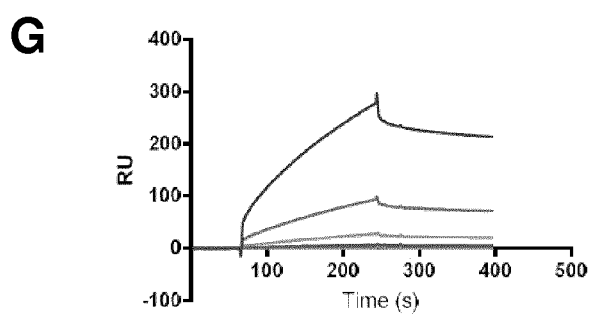

FIG. 3. Surface plasmon resonance (SPR) analysis.
SPR sensorgrams of chimeric E4NG Fab fragment (A), E4 (B), F3(C), D10 (D), and B2 (E) binding to immobilized CEP1. Response Units (R.U.) reflect the result of subtracting CEP1 channel results from REP1 channel. A series of analyte concentrations were tested. The binding of E4NG (F) and F3 (G) to citrullinated Histone2A peptide were analyzed in a similar way as shown in (A)-(E).

Figure 4:
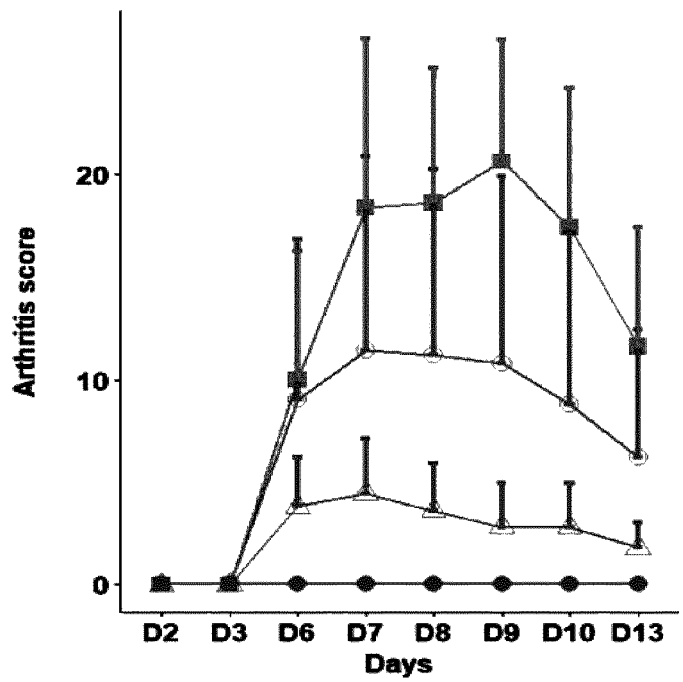
Figure 4:
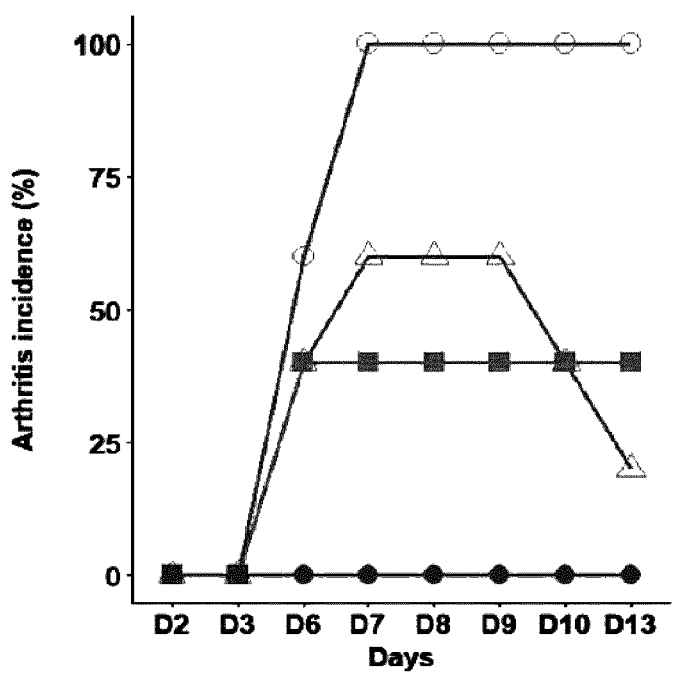
Figure 4:
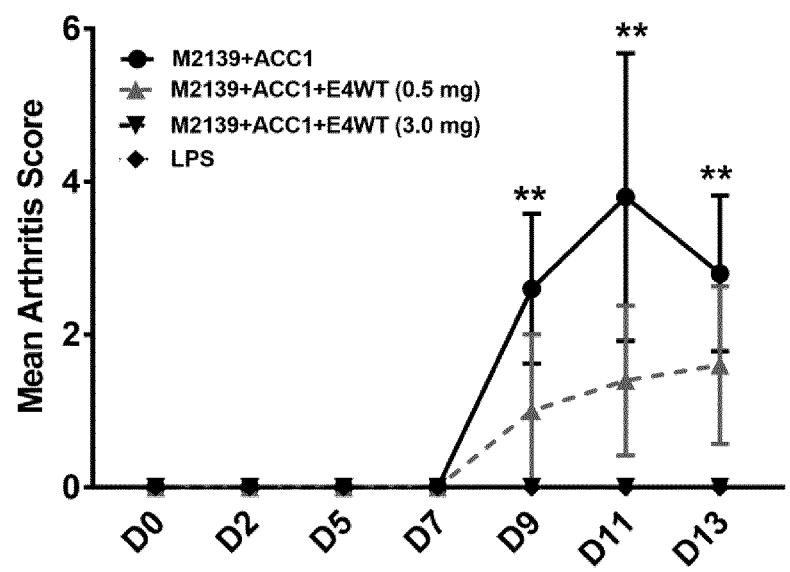
Figure 4:
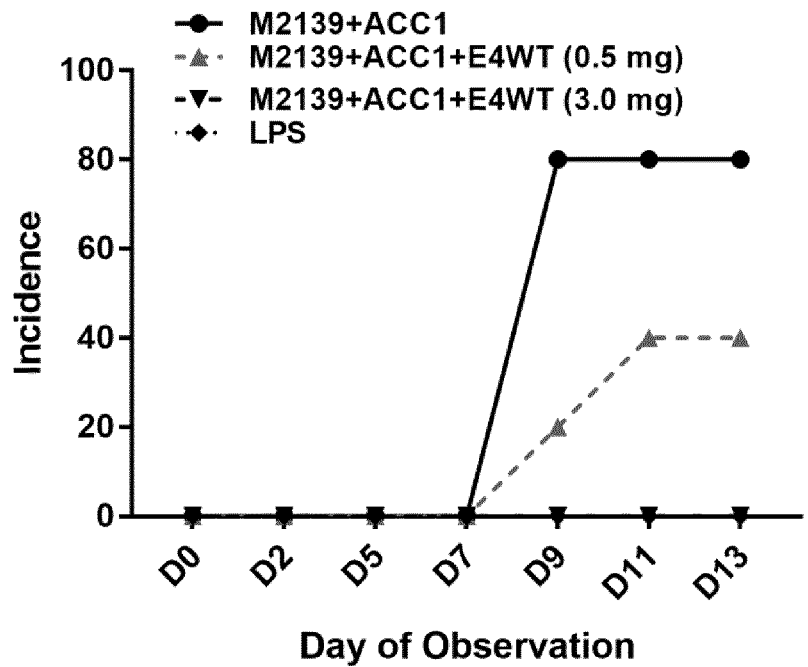

FIG. 4. Evaluation of ACPAs in CAIA model. Experimental animals (Cia9i for A and B, n=5 or 6) were injected with 6 mg of Abs (either single Ab or mixture of Abs as indicated) on day 0 and LPS was given on Day 3 for boosting the disease. CAIA severity (A) and incidence (B) were evaluated until Day 13.
-○—ACC1(3 mg+M2139(3 mg), -△—F3(3 mg)+M2139(3 mg),
-■—M2139(3 mg)+M2139mut(3 mg), -●—chimeric E4NG(3 mg)+M2139(3 mg).
CAIA severity (C) and incidence (D) were evaluated until Day 13.
-▼—M2139+ACC1+E4WT(3.0 mg), -▲-M2139+ACC1+E4WT (0.5 mg),
-●—M2139+ACC1-◆—LPS.

Figure 5:
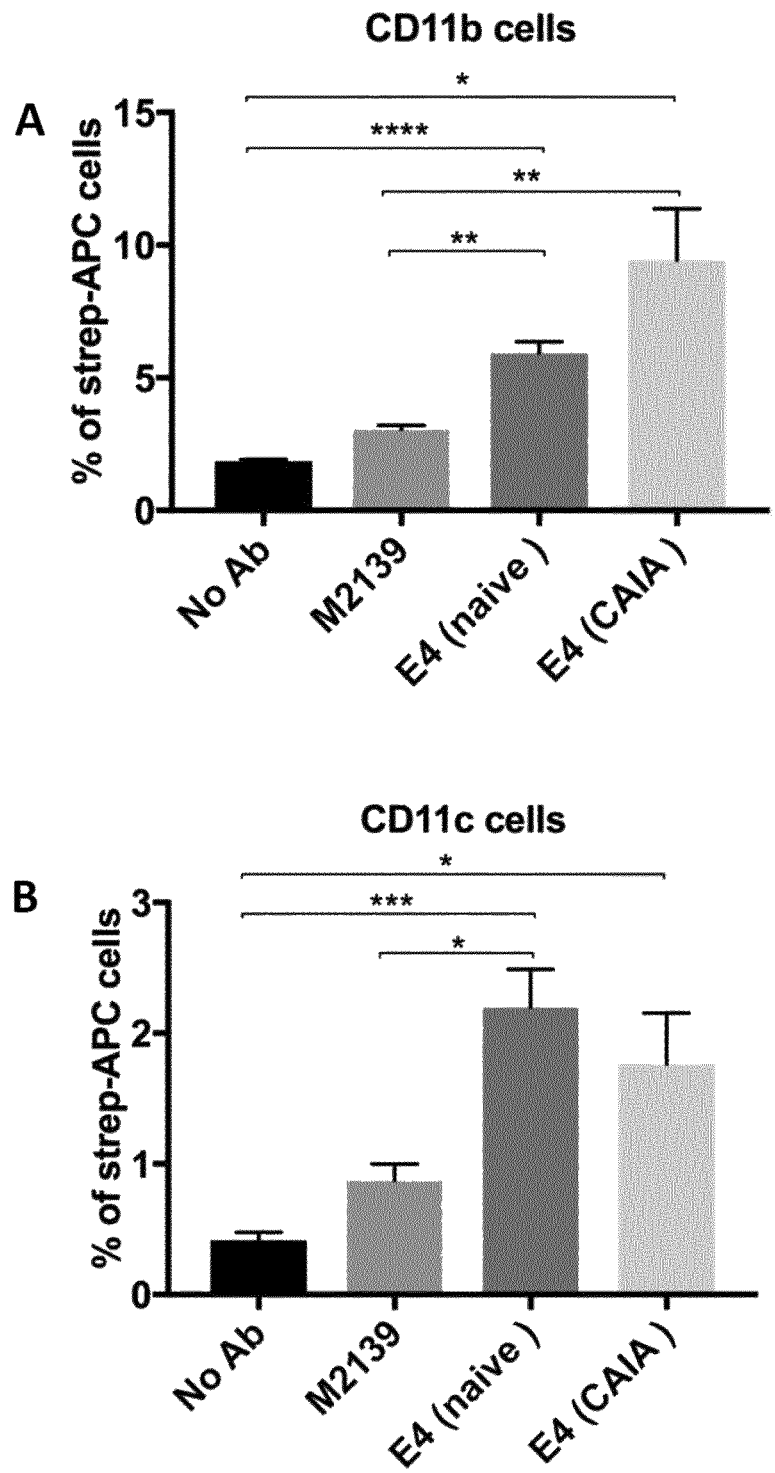
Figure 5:
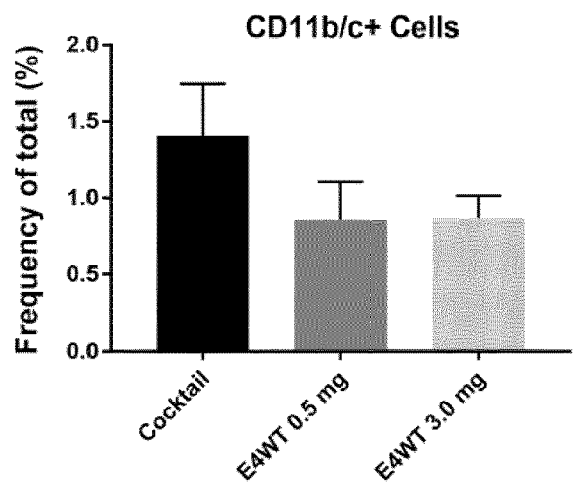
Figure 5:
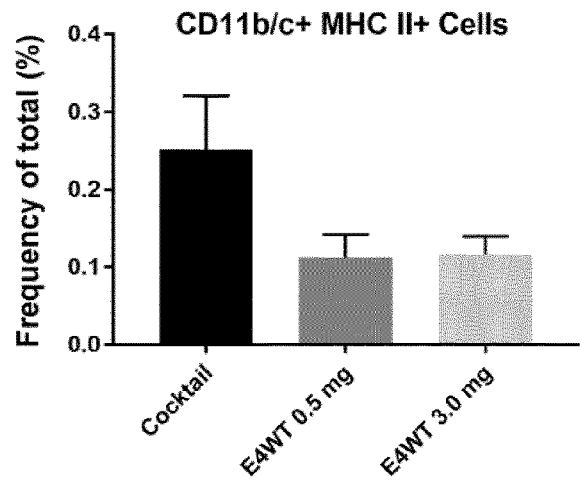
Figure 5:
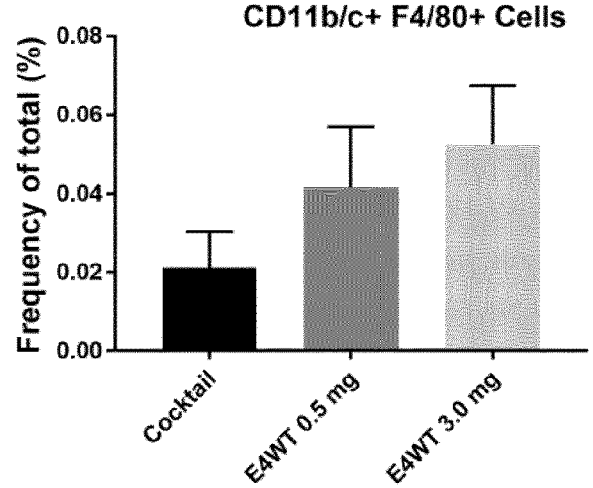

FIG. 5. Characterization of cellular targets of E4. FACS analysis of splenocytes of naive mice injected with biotinylated chimeric E4NG (n=3), biotinylated M2139 (n=3), and arthritic mice (CAIA model (n=3), injected with biotinylated chimeric E4NG. The frequencies of CD11 b (A) and CD11c (B) bound with the given antibodies are shown. Graphs show the means and SEM of triplicates. FACS analysis of splenocytes from arthritic mice (CAIA model) with a control cocktail, E4WT (0.5 mg) and E4WT (3.0 mg). The frequencies of CD11b/c (C), CD11b/c MHCII (D) and CD11b/c F4/80 (E) are shown.

Figure 6:
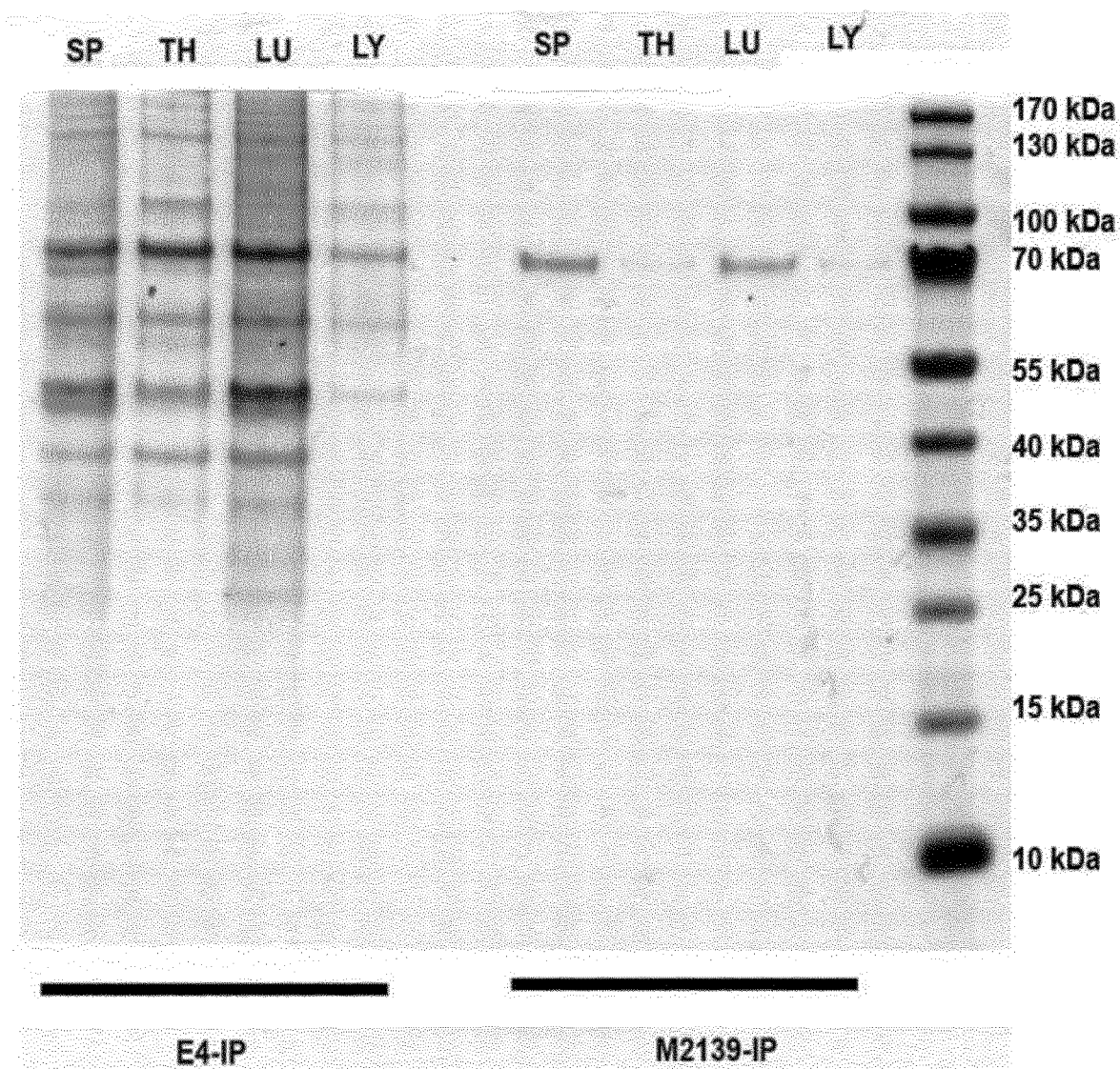

FIG. 6. Cellular targets of E4. Immunoprecipitation of proteins extracted from spleen, thymus, lymph node, and lung by Dynabeads™ (Life Technologies) coated by chimeric E4NG or M2139 via amine coupling. The protein bands were visualized with silver stain. SP: spleen, TH: thymus, LU: lung, LY: lymph node.

FIG. 7. Autoantibody reactivity against CII-13, CII-48 or CEP1. The antibody response to the given peptides in human serum samples from EIRA cohort (A) and TIRA2 cohort (B) was analyzed by Luminex immunoassay. The median fluorescence intensity (MFI) ratio (normalized by a set of reference peptides) was used to quantify the interaction of serum antibody with given peptides. The dotted line indicates the cutoff value for positivity as described in Material and Methods. Mann-Whitney U test was used to calculate p values for differences between groups (****p<0.0001). MFI, median fluorescence intensity; RA, rheumatoid arthritis; HC, healthy controls. The red line indicates the cutoff (median+5×MAD) based on healthy controls. (C) Venn diagram showing the overlapping autoantibody responses in RA patients to CII-C-13, CII-C-48, and CEP1 as determined by Luminex immunoassay. The number of peptide-positive patients is indicated.

Figure 8:
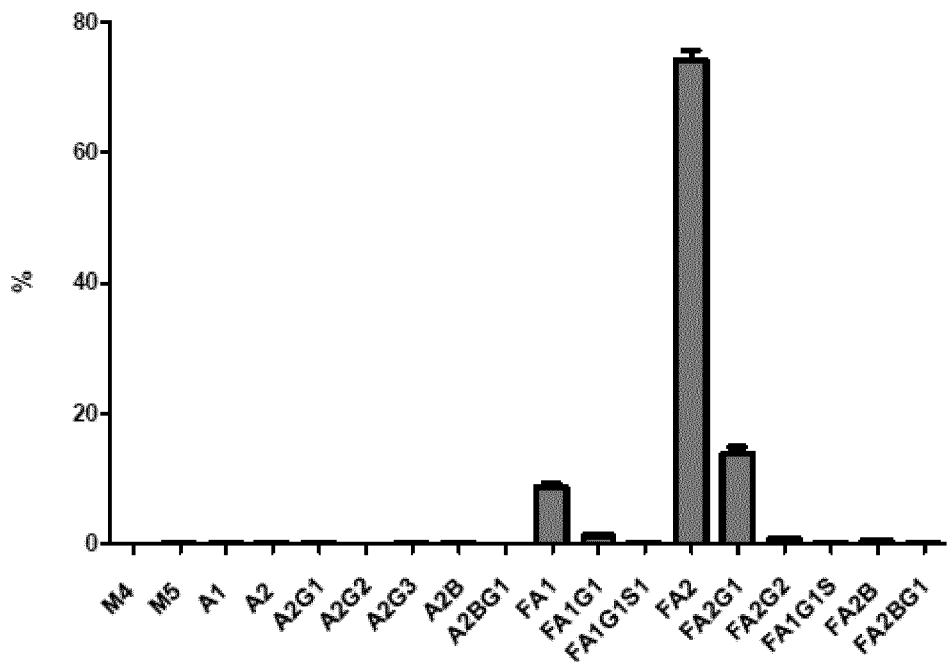
Figure 8:
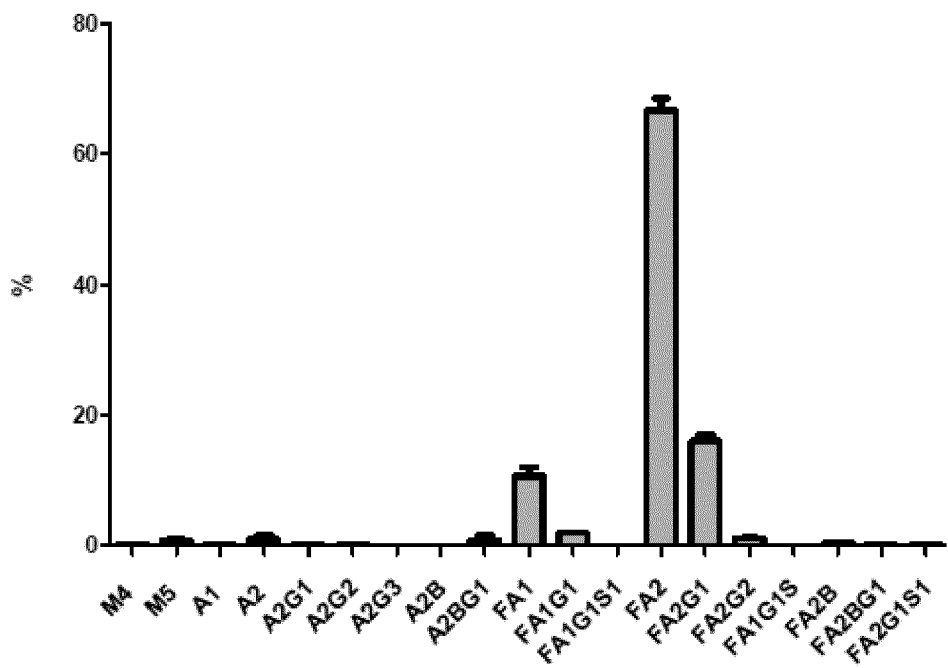

FIG. 8. The Fc-glycosylation pattern of both E4 and F3 analyzed by mass spectroscopy. Bar plot representation of the relative glycan distributions (%) of E4 and F3.

Figure 9:
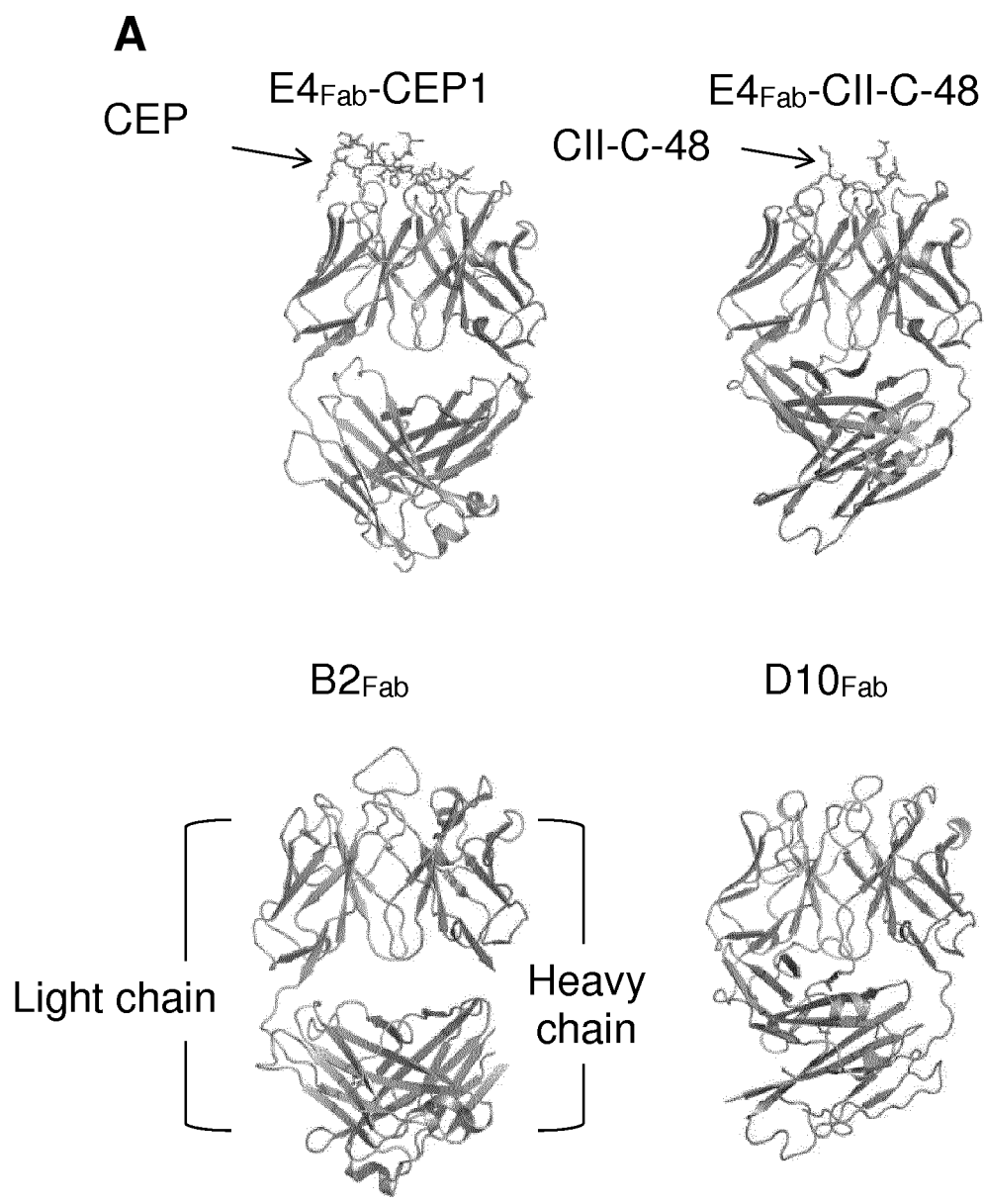
Figure 9:
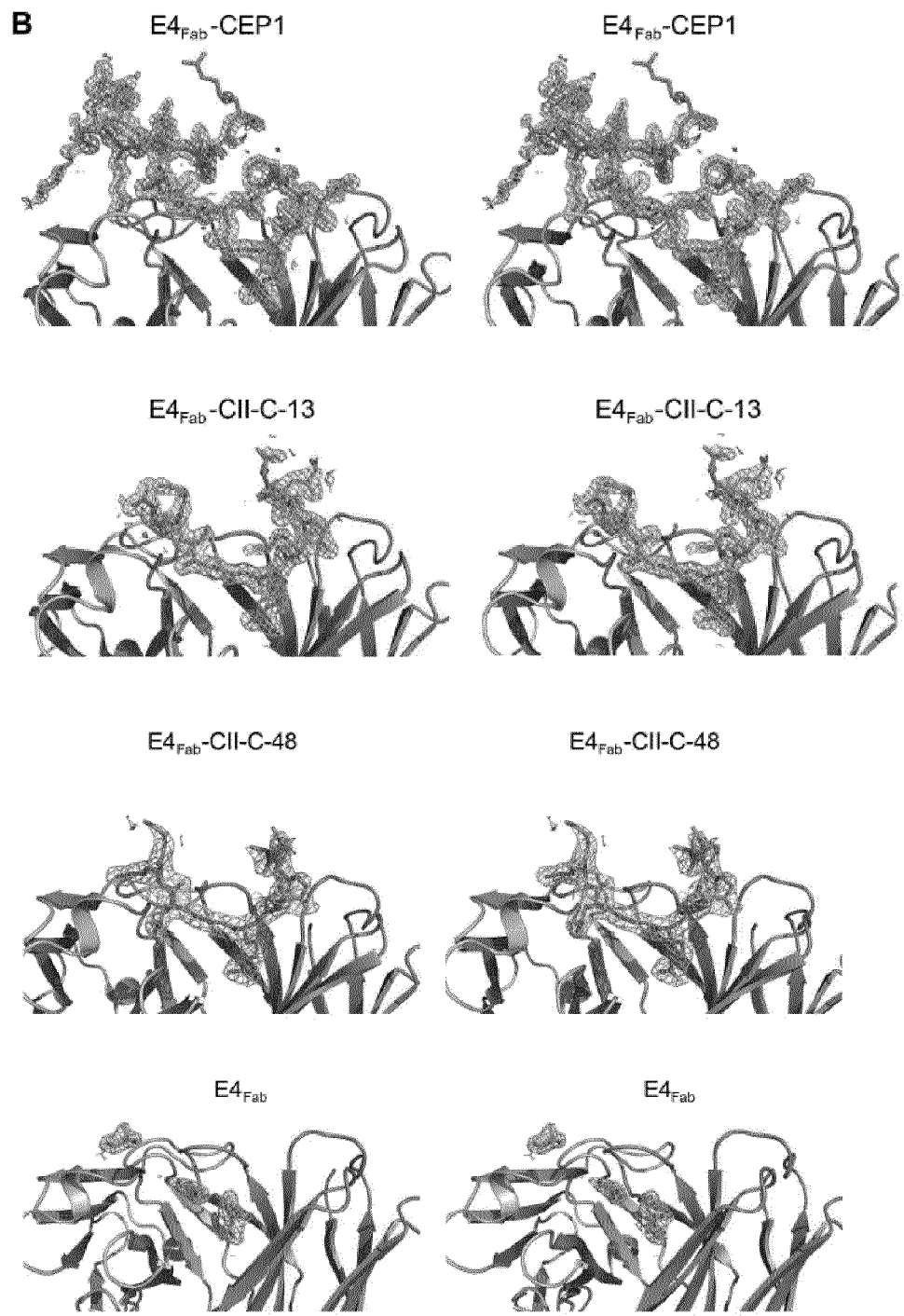

FIG. 9. The crystal structures of $E4_{Fab}$, $B2_{Fab}$, and $D10_{Fab}$. (A) Overall structures of $E4_{Fab}$-CEP1, $E4_{Fab}$-CII-C-48, $B2_{Fab}$ and $D10_{Fab}$ in cartoon representation, with light and heavy chains. Cysteines forming disulfide bridges are shown as sticks. The peptides bound to E4 Fab are shown as sticks with carbon, oxygen, nitrogen, and sulfur atoms colored green, red, blue and yellow, respectively. The structures of $E4_{Fab}$-CII-C-13 and $E4_{Fab}$-CII-C-48 are representative of the crystal structures of $E4_{Fab}$-CII-C-13 and E4 Fab (not shown), respectively, with regard to observed domain orientation. (B) Stereoviews of the E4 Fab paratope and electron density observed for the bounds peptides and glycerol molecules. The final $2F_0$–$F_c$ electron density map (grey) is contoured at 1 σ for a 2 Å radius around the ligands, the $2F_0$-$F_c$ map is contoured at 3σ (green) and –3σ (red).

Figure 10:

FIG. 10. Crystal structure of monoclonal ACPA F3WT. Overall view of F3WT Fab. The F3WT Fab light and heavy constant domains are shown in grey and black, respectively.

DESCRIPTION OF THE INVENTION

The present inventors have analyzed in vivo binding and biological functions of several previously reported monoclonal ACPAs (Uysal et al., 2009). The present inventors demonstrate that these ACPAs specifically recognize the citrulline residue regardless of the peptide epitope sequences. Importantly, one of the characterized ACPA mediates strong protection against experimental arthritis whereas the other had no impact. The protective ACPA targeted cells of myeloid origin, especially the cells expressing CD11c, mainly representing dendritic cells.

Collectively, these results provide insights into the molecular basis for the citrulline specificity and cross-reactivity of ACPAs and demonstrate their significant protective potential in experimental arthritis.

In one aspect, the present invention provides an antibody or antibody fragment capable of binding to a citrullinated peptide,
wherein the antibody or antibody fragment comprises a variable heavy chain (VH) domain and/or a variable light chain (VL) domain, and wherein
(a) the VH domain comprises an amino acid sequence that includes one, two or three complementarity-determining regions (CDRs) selected from the group consisting of:
a CDR1 sequence comprising an amino acid sequence having at least 57%, 71%, 86%, or 100% sequence identity to the sequence of SEQ ID NO: 1 or 2;
a CDR2 sequence comprising an amino acid sequence having at least 56%, 67%, 78%, 89%, or 100% sequence identity to the sequence of SEQ ID NO: 3; and a CDR3 sequence comprising an amino acid sequence having at least 56%, 67%, 78%, 89%, or 100% sequence identity to the sequence of SEQ ID NO: 4 and/or (b) the VL domain comprises an amino acid sequence that includes one, two or three complementarity-determining regions (CDRs) selected from the group consisting of:

a CDR4 sequence comprising an amino acid sequence having at least 50%, 63%, 75%, 88%, or 100% sequence identity to the sequence of SEQ ID NO: 5;

a CDR5 sequence comprising an amino acid sequence having at least 50%, 67%, 83%, or 100% sequence identity to the sequence of SEQ ID NO: 6;

a CDR6 sequence comprising an amino acid sequence having at least 50%, 63%, 75%, 88%, or 100% sequence identity to the sequence of SEQ ID NO: 7.

In one embodiment according to the above aspect of the present invention, the antibody or antibody fragment comprises a VH domain that comprises an amino acid sequence that includes a CDR1 sequence, a CDR2 and a CDR3 sequence as defined above, and/or the VL domain comprises an amino acid sequence that includes a CDR4 sequence, a CDR5 and a CDR6 sequence as defined above.

In a further embodiment of the above aspect of the present invention, the antibody or antibody fragment comprises a VH domain that comprises an amino acid sequence that includes all three of the CDR1, CDR2 and CDR3 sequences present in the amino acid sequence SEQ ID NO: 8, 9, 10, or 11, or an amino acid sequence having at least 80%, 85%, 90%, or 95% sequence identity to the amino acid sequence SEQ ID NO: 8, 9, 10,11, 23 or 24; and/or a VL domain that comprises an amino acid sequence that includes all three of the CDR4, CDR5 and CDR6 sequences present in the amino acid sequence SEQ ID NO: 12 or 13, or an amino acid sequence having at least 80%, 85%, 90%, or 95% sequence identity to the amino acid sequence SEQ ID NO: 12 or 13.

In a further embodiment of the present invention, the antibody or antibody fragment comprises a variable heavy chain (VH) domain and/or a variable light chain (VL) domain, and wherein the VH domain comprises the amino acid sequence SEQ ID NO: 8, 9, 10, or 11, or an amino acid sequence having at least 50%, 60%, 70%, 80%, 85%, 90%, or 95% sequence identity to the amino acid sequence SEQ ID NO: 8, 9, 10, 11, 23 or 24; and the VL domain comprises the amino acid sequence SEQ ID NO: 9 or 10, or an amino acid sequence having at least 50%, 60%, 70%, 80%, 85%, 90%, or 95% sequence identity to the amino acid sequence SEQ ID NO: 12 or 13.

SEQ ID NO: 8 is the variable heavy (VH) domain of the E4NG antibody as described in the following examples, and has the sequence:

QVQLEESGPGLVRPSETLSLSCTVSGFPMSESYFWGWIRQSPGKGLE

WLGSVIHTGTTYYRPSLESRLTIAMDPSKNQVSLSLTSVTVADSAMY

YCVRSVIHTGTTYDPWGPGIVVTVSS and includes the complementarity-determining regions (CDRs):

```
VH CDR1:
                                          (SEQ ID NO: 1)
SESYFWG;

VH CDR2:
                                          (SEQ ID NO: 3)
SVIHTGTTY;

VH CDR3:
                                          (SEQ ID NO: 4)
IRGGSSNWL;
```

SEQ ID NO: 9 is the variable heavy (VH) domain of the E4WT antibody as described in the following examples, and has the sequence:

QVQLEESGPGLVRPSETLSLSCTVSGFPMNESYFWGWIRQSPGKGLE

WLGSVIHTGTTYYRPSLESRLTIAMDPSKNQVSLSLTSVTVADSAMY

YCVRSVIHTGTTYDPWGPGIVVTVSS and includes the complementarity-determining regions (CDRs):

```
VH CDR1:
                                          (SEQ ID NO: 2)
NESYFWG;

VH CDR2:
                                          (SEQ ID NO: 3)
SVIHTGTTY;

VH CDR3:
                                          (SEQ ID NO: 4)
IRGGSSNWL;
```

SEQ ID NO: 10 is the variable heavy (VH) domain of the chimeric E4NG antibody as described in the following examples, and has the sequence:

QVQLEESGPGLVRPSETLSLSCTVSGFPMSESYFWGWIRQSPGKGLE

WLGSVIHTGTTYYRPSLESRLTIAMDPSKNQVSLSLTSVTVADSAMY

YCVRSVIHTGTTYDPWGPGIVVTASS and includes the complementarity-determining regions (CDRs):

```
VH CDR1:
                                          (SEQ ID NO: 1)
SESYFWG;

VH CDR2:
                                          (SEQ ID NO: 3)
SVIHTGTTY;

VH CDR3:
                                          (SEQ ID NO: 4)
IRGGSSNWL;
```

SEQ ID NO: 11 is the variable heavy (VH) domain of the chimeric E4 antibody as described in the following examples, and has the sequence:

QVQLEESGPGLVRPSETLSLSCTVSGFPMNESYFWGWIRQSPGKGLE

WLGSVIHTGTTYYRPSLESRLTIAMDPSKNQVSLSLTSVTVADSAMY

YCVRSVIHTGTTYDPWGPGIVVTASS and includes the complementarity-determining regions (CDRs):

```
VH CDR1:
                         (SEQ ID NO: 2)
    NESYFWG;

VH CDR2:
                         (SEQ ID NO: 3)
    SVIHTGTTY;

VH CDR3:
                         (SEQ ID NO: 4)
    IRGGSSNWL;
```

SEQ ID NO: 23 is the variable heavy (VH) domain of the chimeric E4NG antibody, and has the sequence:

QVQLEESGPGLVRPSETLSLSCTVSGFPMSESYFWGWIRQSPGKGLEWLG
SVIHTGTTYYRPSLESRLTIAMDPSKNQVSLSLTSVTVADSAMYYCVRIR
GGSSNWLDPWGPGIVVTASS and includes the complementarity-determining regions (CDRs):

```
VH CDR1:
                         (SEQ ID NO: 2)
    NESYFWG;

VH CDR2:
                         (SEQ ID NO: 3)
    SVIHTGTTY;

VH CDR3:
                         (SEQ ID NO: 4)
    IRGGSSNWL;
```

SEQ ID NO: 24 is the variable heavy (VH) domain of the chimeric E4NG antibody, and has the sequence:

QVQLEESGPGLVRPSETLSLSCTVSGFPMSESYFWGWIRQSPGKGLEWLG
SVIHTGTTYYRPSLESRLTIAMDPSKNQVSLSLTSVTVADSAMYYCVRIR
GGSSNWLDPWGPGIVVTVSS and includes the complementarity-determining regions (CDRs):

```
VH CDR1:
                         (SEQ ID NO: 2)
    NESYFWG;

VH CDR2:
                         (SEQ ID NO: 3)
    SVIHTGTTY;

VH CDR3:
                         (SEQ ID NO: 4)
    IRGGSSNWL;
```

SEQ ID NO: 12 is the variable light (VL) domain of the E4NG antibody and has the sequence:

QSVWTQPPSVSAAPGQKVTISCSGDDSILRSAFVSWYQQVPGSAPKLVIF
DDRQRPSGIPARFSGSNSGTTATLDIAGLQRGDEADYYCAAWNGRLSAFV
FGSGTTVSVLRT and includes the complementarity-determining regions (CDRs):

```
VL CDR4:
                         (SEQ ID NO: 5)
    DSILRSAF;

VL CDR5:
                         (SEQ ID NO: 6)
    DDRQRP;

VL CDR6:
                         (SEQ ID NO: 7)
    WNGRLSAF,
```

SEQ ID NO: 13 is the variable light (VL) domain of the E4WT antibody and has the sequence:

QSVWTQPPSVSAAPGQNVTISCSGDDSILRSAFVSWYQQVPGSAPKLVIF
DDRQRPSGIPARFSGSNSGTTATLDIAGLQRGDEADYYCAAWNGRLSAFV
FGSGTTVSVLRT and includes the complementarity-determining regions (CDRs):

```
VL CDR4:
                         (SEQ ID NO: 5)
    DSILRSAF;

VL CDR5:
                         (SEQ ID NO: 6)
    DDRQRP;

VL CDR6:
                         (SEQ ID NO: 7)
    WNGRLSAF,
```

SEQ ID NO: 14 is the variable light (VL) domain of the chimeric E4NG antibody and has the sequence:

QSVWTQPPSVSAAPGQKVTISCSGDDSILRSAFVSWYQQVPGSAPKLVIF
DDRQRPSGIPARFSGSNSGTTATLDIAGLQRGDEADYYCAAWNGRLSAFV
FGSGTKLTVLG and includes the complementarity-determining regions (CDRs):

```
VL CDR4:
                         (SEQ ID NO: 5)
    DSILRSAF;

VL CDR5:
                         (SEQ ID NO: 6)
    DDRQRP;

VL CDR6:
                         (SEQ ID NO: 7)
    WNGRLSAF,
```

SEQ ID NO: 15 is the variable light (VL) domain of the chimeric E4WT antibody and has the sequence:

```
QSVWTQPPSVSAAPGQNVTISCSGDDSILRSAFVSWYQQVPGSAPKLVIF
DDRQRPSGIPARFSGSNSGTTATLDIAGLQRGDEADYYCAAWNGRLSAFV
FGSGTKLTVLG
``` and includes the complementarity-determining regions (CDRs):

VL CDR4:
(SEQ ID NO: 5)
DSILRSAF;

VL CDR5:
(SEQ ID NO: 6)
DDRQRP;

VL CDR6:
(SEQ ID NO: 7)
WNGRLSAF,

In a further embodiment, the antibody or antibody fragment is based on the VH and/or VL domains of the E4 antibodies, and so
- the VH domain (i) comprises an amino acid sequence having at least 80%, 85%, 90%, 95% or 100% sequence identity SEQ ID NO: 8, 9, 10, or 11 and/or (ii) comprises a CDR1 sequence comprising an amino acid sequence having at least 57%, 71%, 86%, or 100% sequence identity to the sequence of SEQ ID NO: 1 or 2, a CDR2 sequence comprising an amino acid sequence having at least 56%, 67%, 78%, 89%, or 100% sequence identity to the sequence of SEQ ID NO: 3, and a CDR3 sequence comprising an amino acid sequence having at least 56%, 67%, 78%, 89%, or 100% sequence identity to the sequence of SEQ ID NO: 4; and/or
- the VL domain (iii) comprises an amino acid sequence having at least 80%, 85%, 90%, 95% or 100% sequence identity SEQ ID NO: 12, 13, 14, or 15 and/or (iv) a CDR4 sequence comprising an amino acid sequence having at least 50%, 63%, 75%, 88%, or 100% sequence identity to the sequence of SEQ ID NO: 5, a CDR5 sequence comprising an amino acid sequence having at least 50%, 67%, 83%, or 100% sequence identity to the sequence of SEQ ID NO: 6, and a CDR6 sequence comprising an amino acid sequence having at least 50%, 63%, 75%, 88%, or 100% sequence identity to the sequence of SEQ ID NO: 7.

It may be preferred that the VH domain comprises the sequence of SEQ ID NO: 8 and the VL domain comprises the sequence of SEQ ID NO: 12.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. Exemplary human CH regions for use in this context include:

```
(SEQ ID NO: 16)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK.
```

SEQ ID NO: 16 is the sequence of the CH region of Human IgG1 (UniProtKB/Swiss-Prot: P01857.1). Optionally, the terminal K (Lys) in the CH region of SEQ ID NO: 16 may be removed, which reduces or avoids the potential for peptidase degradation.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes:

```
(SEQ ID NO: 17)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC
```

SEQ ID NO: 17 is the sequence of the CL region of Human kappa constant region (UniProtKB/Swiss-Prot: P01834.2)

Another exemplary human CL region for use in this context includes:

```
(SEQ ID NO: 18)
GQPKAAPSVTLFPPSSEELQANKATLVCLISDFYPGAVTVAWKADSSPVK
AGVETTTPSKQSNNKYAASSYLSLTPEQWKSHKSYSCQVTHEGSTVEKTV
APTECS.
```

SEQ ID NO: 18 is the sequence of the CL region of Human lambda constant region (UniProtKB/Swiss-Prot: P0DOY3.1).

According to this embodiment, it may be preferred that the VH domain comprises the sequence of SEQ ID NO: 8, linked to the CH region of SEQ ID NO: 16 and the VL domain comprises the sequence of SEQ ID NO: 12 linked to the CL region of SEQ ID NO: 17.

The antibody or antibody fragment of this embodiment may further comprise a heavy chain constant (CH) region or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region. The CH region or a fragment thereof may be joined to the VH domain. There is no particular limitation on the CH region although in one embodiment it is a human CH region. The art contains many examples of human CH regions. An exemplary human CH region for use in this context includes SEQ ID NO: 16.

In one embodiment, the Fc region and/or the Fab region is glycosylated. In one embodiment, the CH region and/or the VH region is glycosylated. The said regions may be glycosylated at one or more sites so that one or more carbohydrate moieties are covalently attached to the said regions. Glycosylation sites may be introduced into the constant region of the antibodies of the invention. "Glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N-linkages. N-linked glycosylation refers to the attachment of an oligosaccharide moiety to the side chain of an asparagine residue. The antibodies of the invention may comprise one or more glycosylation sites, including N-linked glycosylation sites. Any glycosylation site for N-linked known in the art may be used in accordance with the present invention.

The antibody or antibody fragment of this embodiment may additionally, or alternatively further comprise a light chain constant (CL) region or a fragment thereof which fragment may comprise, for example, at least 10, 20, 30, 40, 50, 60, 70, 80, 90, 100 or more amino acids of a CL region. The CL region or a fragment thereof may be joined to the VL domain. There is no particular limitation on the CL region although in one embodiment it is a human CL region. The art contains many examples of human CL regions. An exemplary human CL region for use in this context includes SEQ ID NO: 17 or 18.

In the various foregoing embodiments, the discussion of CH regions and fragments thereof is also intended to include the option of using a variant of either. The variant comprises a sequence having less than 100% sequence identity to the stated CH region or fragment thereof, such as greater than 50%, 60%, 70%, 80%, 85%, 90%, 95%, 96%, 97%, 98%, or 99% sequence identity. Accordingly, variants of a CH region or a fragment thereof may possess one or more (such as 2, 3, 4, 5, 6, 7, 8, 9, 10, 15, 20, 25, 30, 40, 50, 60, 70 80, 90, 100, 110, 120, 130, 140, 150 160 or more) sequence variations compared to the stated CH region or fragment thereof. Variations in the sequence may be due to one or more amino acid additions, one or more amino acid deletions and/or one or more amino acid substitutions compared to the stated CH region or fragment thereof. Where there is more than one variation, then the variations may be in consecutive or non-consecutive positions.

Likewise, in the various foregoing embodiments, the discussion of CL regions and fragments thereof is also intended to include the option of using a variant of either. The variant comprises a sequence having less than 100% sequence identity to the stated CL region or fragment thereof, such as greater than 50%, 60%, 70%, 80%, 85%, 90%, 95%, 96%, 97%, 98%, or 99% sequence identity. Accordingly, variants of a CL region or a fragment thereof may possess one or more (such as 2, 3, 4, 5, 6, 7, 8, 9, 10, 15, 20, 25, 30, 40, 50, 60 or more) sequence variations compared to the stated CL region or fragment thereof. Variations in the sequence may be due to one or more amino acid additions, one or more amino acid deletions and/or one or more amino acid substitutions compared to the stated CL region or fragment thereof. Where there is more than one variation, then the variations may be in consecutive or non-consecutive positions.

In the antibody or antibody fragment according to the foregoing embodiments, it may be preferred that the VH domain, the VL domain, or preferably both of the VH and VL domains, comprise an amino acid sequence having 100% sequence identity to the, or in the case of stated SEQ ID NOs that correspond to individual CDR sequences than one or more (such as, two or three) of each, stated SEQ ID NO.

Thus, for example, a preferred antibody or antibody fragment according to the foregoing embodiments that are based on the E4NG antibody may comprise a VH domain comprising the sequence of SEQ ID NO:8 and/or a VL domain comprising the sequence of SEQ ID NO:12.

In another embodiment, a preferred antibody or antibody fragment according to the foregoing embodiments that are based on the E4NG antibody may comprise a VH domain comprising the sequence of SEQ ID NO:23 and/or a VL domain comprising the sequence of SEQ ID NO:14.

In another embodiment, a preferred antibody or antibody fragment according to the foregoing embodiments that are based on the E4NG antibody may comprise a VH domain comprising the sequence of SEQ ID NO:23 and/or a VL domain comprising the sequence of SEQ ID NO:12.

In another embodiment, a preferred antibody or antibody fragment according to the foregoing embodiments that are based on the E4NG antibody may comprise a VH domain comprising the sequence of SEQ ID NO:24 and/or a VL domain comprising the sequence of SEQ ID NO:14.

In another embodiment, a preferred antibody or antibody fragment according to the foregoing embodiments that are based on the E4NG antibody may comprise a VH domain comprising the sequence of SEQ ID NO:24 and/or a VL domain comprising the sequence of SEQ ID NO:12.

Alternatively, in another embodiment, an antibody or antibody fragment according to the foregoing embodiments may comprise a VH domain, a VL domain, or both of the VH and VL domains, that each comprises an amino acid sequence having less than 100% sequence identity to the, or in the case of stated SEQ ID NOs that correspond to individual CDR sequences than one or more (such as, two or three) of each, stated SEQ ID NO.

In accordance with the first aspect of the present invention, a sequence comprising an amino acid sequence having less than 100% sequence identity to the stated SEQ ID NO may be a sequence possessing one or more (such as 2, 3, 4, 5, 6, 7, 8, 9, 10 or more) sequence variations compared to the stated SEQ ID NO. Variations in sequence may be due to one or more (such as 2, 3, 4, 5, 6, 7, 8, 9, 10 or more) amino acid additions, one or more (such as 2, 3, 4, 5, 6, 7, 8, 9, 10 or more) amino acid deletions and/or one or more (such as 2, 3, 4, 5, 6, 7, 8, 9, 10 or more) amino acid substitutions compared to the stated SEQ ID NO. Where there is more than one variation, then the variations may be in consecutive or non-consecutive positions.

The one or more variations in sequence in a variant antigen binding region that has less than 100%, but at least 80%, 85%, 90%, 95%, sequence identity to a stated SEQ ID NO selected from SEQ ID NOs: 8-15 may be present in, or exclusively in, the amino acid sequence that forms one or more of the framework regions. Framework regions comprise the amino acid regions that do not form the CDRs as defined herein.

Additionally or alternatively, one or more variations in sequence in an antigen binding region that has less than 100%, but at least 80%, 85%, 90%, 95%, sequence identity to a stated SEQ ID NO selected from SEQ ID NOs: 8-15 may be present in, or exclusively in, the amino acid sequence that form one or more of the complementarity-determining regions (CDRs). The CDRs in SEQ ID NOs: 8-15 are as defined above by reference to SEQ ID NOs: 1-7.

In all embodiments of the above aspects of the invention, in general, higher levels of sequence modifications may be tolerated in the framework regions than in the CDRs without substantially altering the binding characteristics and/or in vivo efficacy of the antibody or antibody fragment.

Thus, for example, in a further embodiment, a, the, or each, CDR in an antibody or antibody fragment according to the first aspect of the present invention may comprise up to 1, 2, 3, 4, 5, 6, 7, 8, 9 or 10 amino acid substitutions, insertions and/or deletions compared to the 'parent' CDR sequence defined one of SEQ ID NOs 8 to 15 and preferably not more than 5, 4, 3, 2 or 1 amino acid substitutions, insertions and/or deletions; it may be preferred that the number of amino acid substitutions, insertions and/or deletions implemented in the CDR sequence to not reduce the level of sequence identity to less than 50%, 60%, 70%, 75%, 80%, 85%, 90%, 95% compared to the corresponding defined SEQ ID NO.

Additionally, and/or alternatively, a, the, or each, framework region in an antibody or antibody fragment according to the first aspect of the present invention may comprise up to 1, 2, 3, 4, 5, 6, 7, 8, 9, 10, 11, 12, 13, 14, 15, 16, 17, 18, 19, 20, or more amino acid substitutions, insertions and/or deletions compared to the corresponding framework sequence present in any of the VH or VL sequences defined SEQ ID NOs 8 to 15, and optionally not more than 10, 9, 8, 7, 6, 5, 4, 3, 2 or 1 amino acid substitutions, insertions and/or deletions; it may be preferred that the number of amino acid substitutions, insertions and/or deletions implemented in any framework region to not reduce the level of sequence identity to less than 10%, 20%, 30%, 40% 50%, 60%, 70%, 75%, 80%, 85%, 90%, 95% compared to the corresponding defined SEQ ID NO.

Substitutions, whether in one or more of the framework or complementarity determining regions, may be conservative or non-conservative substitutions. By "conservative substitutions" is intended combinations such as Gly, Ala; Val, Ile, Leu; Asp, Glu; Asn, Gln; Ser, Thr; Lys, Arg; and Phe, Tyr.

Sequence variations may, for example, be introduced in order to render the sequence of the antigen binding region(s) closer to germline sequences, to improve the stability of the antibody or antibody fragment comprising the variant antigen binding region(s), to reduce the immunogenicity of the antibody or antibody fragment comprising the variant antigen binding region(s), and/or to avoid or reduce properties that could be disadvantageous in the manufacturing process.

Such variants may be made using the methods of protein engineering and site-directed mutagenesis as described below or alternative methods that are well known in the art.

Where the VH domain, the VL domain, or both of the VH and VL domains, of the antibody or antibody fragment of the first aspect of the present invention comprise(s) one or more amino acid sequence having less than 100% sequence identity to the, or one or more of each, stated SEQ ID NO, then in one embodiment the ability of the antibody or antibody fragment to bind to a citrullinated peptide may, for example, be substantially equivalent to (that is, at least 80%, 85%, 90% or 95%, of), or greater than, the ability of a corresponding 'parent' antibody or antibody fragment, wherein the VH domain and the VL domain of the corresponding 'parent' antibody or antibody fragment each comprise an antigen-binding sequence comprising an amino acid sequence having 100% sequence identity to the, or each, stated SEQ ID NO.

Thus, for example, where the antibody or antibody fragment is based on the E4 antibody, and the VH domain comprises an antigen-binding sequence comprising an amino acid sequence having less than 100%, but at least 80%, 85%, 90%, or 95% sequence identity SEQ ID NO:8; and/or the VL domain comprises an antigen-binding sequence comprising an amino acid sequence having less than 100%, but at least 80%, 85%, 90%, or 95% sequence identity SEQ ID NO: 12, then the ability of the antibody or antibody fragment to bind to a citrullinated peptide, for example, be equivalent to the binding ability of a corresponding 'parent' antibody or antibody fragment having a VH domain that comprises the sequence of SEQ ID NO:8 and a VL domain that comprises the sequence of SEQ ID NO: 12. In this context, by "corresponding 'parent' antibody or antibody fragment" is meant that the only sequence difference between the "antibody or antibody fragment" in hand and the "corresponding 'parent' antibody or antibody fragment" is in one or both of the antigen-binding sequences of the VH and/or VL domain. In one embodiment, the corresponding parent antibody is an antibody having the sequence of the VH, VL, CH and CL regions of E4NG, that is, a VH domain of SEQ ID NO: 8 linked to the CH region of SEQ ID NO: 16 and the VL domain of SEQ ID NO: 12 linked to the CL region of SEQ ID NO: 17.

The same applies, mutatis *mutandis*, to the other antibody or antibody fragment listed above wherein the VH and/or VL domains comprise(s) one or more amino acid sequences having less than 100% sequence identity to the, or one or more of each, stated SEQ ID NO, and the "corresponding 'parent' antibody or antibody fragment" for the purposes of determining binding equivalence to a citrullinated peptide differs only in the one or both of the VH and/or VL domain and possess(es) the, or each, antigen-binding sequences comprising an amino acid sequence having 100% sequence identity to the, or each, stated SEQ ID NO.

In this regard, the ability of an antibody or antibody fragment to bind to a citrullinated peptide may be determined by any suitable method, such as by Surface Plasmon Resonance (SPR) analysis, to measure the binding of the antibody or antibody fragment to a citrullinated peptide immobilized to a solid surface such as the Biacore SPR biosensor.

As discussed in the examples below, E4NG binds immobilized citrullinated peptide CEP1 with a Kd of 0.25 nM. In one embodiment, an antibody or antibody fragment according to the present invention will bind immobilized citrullinated peptide CEP1 with an apparent Kd of no greater than about 1 nM, about 0.9 nM, about 0.8 nM, about 0.7 nM, about 0.6 nM, about 0.5 nM, about 0.4 nM, about 0.3 nM, about 0.25 nM, or less when tested under conditions (such as the SPR conditions used in the examples) that provide for binding of an antibody or antibody fragment having the VH and VL domains of E4NG (as defined by SEQ ID NOS 8 and 12, respectively) to immobilized citrullinated peptide CEP1 with an apparent Kd of about 300 nM. In this context, the term "about" is used to mean a value that is within ±20%, 15%, 10%, 5%, 4%, 3%, 2%, or 1% of the stated value.

In an additional embodiment, an antibody or antibody fragment according to the first aspect of the present invention competes with a 'comparator' antibody or antibody fragment for binding to a citrullinated peptide as defined herein (e.g., as determined in an ELISA or SPR assay). In this context, a comparator antibody or antibody fragment may comprise the VH and VL domains, and optionally also the CH and CL domains, of E4NG (as defined by SEQ ID NOs: 8, 12, 16, and 17, respectively), and preferably differs from the antibody or antibody fragment being tested only by sequence variation in the VH and/or VL regions. By 'competes', we mean that inclusion of equimolar amounts of the antibody or antibody fragment according to the first aspect of the present invention and the 'comparator' antibody in an assay can reduce the detectable level of binding to a citrullinated peptide of the comparator antibody by 10% 20%, 30%, 40%, 50%, 60%, 70%, 80%, 90%, 95% or more, such as substantially 100%, in comparison to the detectable level of binding to a citrullinated peptide of the 'comparator' antibody in the same assay in the absence of the antibody or antibody fragment according to the first aspect of the present invention.

As also discussed in the examples below, chimeric E4NG can protect against collagen antibody-induced arthritis (CAIA) in mice. In another embodiment, an antibody or antibody fragment according to the present invention will protect against collagen antibody-induced arthritis (CAIA) in mice when tested under conditions (such as described in the example below) that provide for protection against collagen antibody-induced arthritis (CAIA) in mice of an antibody or antibody fragment having the VH and VL domains of E4NG (as defined by SEQ ID NOs: 10 and 14, respectively). In this context, the term "about" is used to mean a value that is within ±20%, 15%, 10%, 5%, 4%, 3%, 2%, or 1% of the stated value.

In one embodiment, the antibody or antibody fragment of the present invention may comprise the VH domain and the VL domain in a linear polypeptide sequence.

In another embodiment, the antibody or antibody fragment of the present invention may comprise the VH domain and the VL domain each in a separate polypeptide sequence. In this embodiment, it may be preferred that the separate polypeptide sequence is directly or indirectly bound together (such as by one or more disulfide bonds between the separate polypeptide sequence).

In another embodiment, the VH domain may be joined to a CH region, or a fragment thereof which fragment may comprise, for example, at least 10, 20, 30, 40, 50, 60, 70, 80, 90, 100, 120, 140, 160, 180, 200, 220, 240, 260, 280, 300, 320 or more amino acids of a CH region, or a variant of the CH region or a fragment thereof, as described above. The join may be a direct fusion via a peptide bond, such that the VH domain and CH region are presented as a single polypeptide, or the join may be through a linker, such as a peptide or other linker, or via a direct chemical bond other than a peptide bond. There is no particular limitation on the CH region although in one embodiment it is a human CH region. The art contains many examples of human CH regions. An exemplary human CH regions for use in this context includes SEQ ID NO: 16.

In another embodiment, the VL domain may be joined to a CL region, or a fragment may comprise, for example, at least 10, 20, 30, 40, 50, 60, 70, 80, 90, 100 or more amino acids of a CL region, or a variant of the CL region or a fragment thereof, as described above. The join may be a direct fusion via a peptide bond, such that the VL domain and CL region are presented as a single polypeptide, or the join may be through a linker, such as a peptide or other linker, or via a direct chemical bond other than a peptide bond. There is no particular limitation on the CL region although in one embodiment it is a human CL region. The art contains many examples of human CL regions. An exemplary human CL region for use in this context includes SEQ ID NO: 17 and 18.

In another embodiment, the antibody or antibody fragment of the present invention may comprise a VH domain joined to a CH region in one polypeptide sequence, and a VL domain joined to a CL region in another separate polypeptide sequence. In this embodiment, it may be preferred that the separate polypeptide sequence is directly or indirectly bound together (such as by one or more disulfide bonds between the separate polypeptide sequence).

In a further embodiment, the antibody or antibody fragment of the present invention may comprise
a first heavy chain comprising a first VH domain joined to a first CH region,
a first light chain comprising a first VL domain joined to a first CL region;
a second heavy chain comprising a second VH domain joined to a second CH region,
a second light chain comprising a second VL domain joined to a second CL region; and
wherein optionally, the first light and first heavy chains are directly or indirectly bound together (such as by one or more disulphide bonds between the separate polypeptide sequence) and the second light and second heavy chains are directly or indirectly bound together (such as by one or more disulphide bonds between the separate polypeptide sequence), and further optionally, wherein the first and second heavy chains directly or indirectly bound together (such as by one or more disulphide bonds between the separate polypeptide sequence).

In a further embodiment, the antibody or antibody fragment of the present invention may be a monoclonal antibody, more preferably a human monoclonal antibody.

The antibody or antibody fragment of the present invention may be a humanized antibody or a chimeric antibody.

In one preferred embodiment, the antibody or antibody fragment of the present invention is an isolated antibody or antibody fragment.

In another embodiment, the antibody or antibody fragment of the present invention may comprise one or more of the amino acid sequences comprising the VH, VL, CDR1, CDR2, CDR3, CDR4, CDR5 and/or CDR6 sequences described above grafted onto protein scaffolds of immunoglobulins using standard protein engineering techniques. The skilled person will appreciate that various protein scaffolds are available for use and commonly known in the art. The result is preserved antigen-binding activity in a new framework.

For example, the scaffolds of immunoglobulins can be derived from IgA, IgE, IgG1, IgG2a, IgG2b, IgG3, IgM. The scaffolds can be derived from an immunoglobulin from any mammal, such as mice, rats, rabbits, goats, camels, llamas, primates. It may be preferred that the immunoglobulin scaffold is derived from human immunoglobulins.

The antibody fragments of the present invention can be generated by standard molecular biology techniques or by cleavage of purified antibodies using enzymes (e.g. pepsin or papain) that generates these fragments. Such antibody fragments according to the invention are exemplified, but not limited to, single chain antibodies, Fv, scFv, Fab, F(ab')$_2$, Fab', Fd, dAb, CDR, or scFv-Fc fragments or nanobodies, and diabodies, or any fragment that may have been stabilized by e.g. PEGylation.

In one aspect, the present invention provides a polynucleotide comprising a sequence encoding an antibody or an antibody fragment, or polypeptide chain forming part of the antibody or an antibody fragment, according to the present invention. The polynucleotide may, for example, be DNA or RNA. The polynucleotide may comprise additional sequence 5' and/or 3' to the sequence encoding the, or part of, the antibody or an antibody fragment according to the first aspect of the invention. Such 5' and 3' sequences may include transcriptional and/or translational regulatory sequences, such as promoter and/or terminator sequences which are well known in the art and may, for example, be selected to be functional in a host cell of choice. Accordingly, the polynucleotide may comprise an expression cassette that, following transformation into a host cell of choice, can be expressed by the transcriptional and/or translational systems of the host cell to result in the production of the encoded antibody or an antibody fragment, or polypeptide chain forming part of the antibody or an antibody fragment, according to the first aspect of the invention.

The term "nucleic acid molecule" and "polynucleotide" are herein used interchangeably.

In one aspect, the present invention provides a vector e.g. a plasmid, comprising one or more polynucleotides according to the present invention. Where the antibody or antibody fragment comprises more than one polypeptide chain, the vector may, for example, comprise a polynucleotide encoding each polypeptide chain, such that a host cell transformed with the vector can express all polypeptide chains present in the antibody or antibody fragment. In one embodiment, said vector is a plasmid.

Accordingly, the present invention also provides for the use of a vector in the transformation of a host cell. Methods of transforming host cells with vectors or plasmids are well known in the art. To aid the selection of transformed host cells, the vector or plasmid may comprise a selectable marker.

In another aspect, the present invention provides a host cell comprising one or more vectors or plasmids according to the present invention. The present invention also provides for a culture of cells comprising the one or more vectors or plasmids according to the present invention, such as monoculture in which all or substantially all cells comprise the same one or more vectors or plasmids according to the fifth aspect of the invention. Such monocultures can be obtained, for example, by selecting cells for the presence of one or more selectable markers on the one or more plasmids or vectors and optionally maintaining the selective pressure during the growth of the selected cell in culture.

Where the antibody or antibody fragment according to the present invention comprises more than one polypeptide chain, the host cell may be transformed with a single vector or plasmid that comprises a nucleic acid coding sequence encoding each polypeptide chain, such that a host cell transformed with the vector or plasmid can express all polypeptide chains present in the antibody or antibody fragment.

Alternatively, where the antibody or antibody fragment according to the the present invention comprises more than one polypeptide chain, the host cell may be transformed with more than one vector or plasmid that each comprises a nucleic acid coding sequence encoding at least one of the polypeptide chains, such that a host cell transformed with the more than one vectors or plasmids can express all polypeptide chains present in the antibody or antibody fragment.

In a further alternative, where the antibody or antibody fragment according to the present invention comprises more than one polypeptide chain, multiple host cells may each be transformed with a vector or plasmid that each comprises a different nucleic acid coding sequence each encoding one or more different members of the different polypeptide chains that form the antibody or antibody fragment, and each different host cell cultured separately to express each polypeptide chain. The recovered different polypeptide chains can then be combined to produce the antibody or antibody fragment.

Any suitable host cell can be used in the present invention. For example, the host cell may be a prokaryotic cell, such as an *Escherichia coli* cell. The host cell may be a eukaryotic cell, such as an animal cell, a plant cell, and a fungal cell. Suitable animal cells may include mammalian cells, avian cells, and insect cells. Suitable mammalian cells can include CHO cells and COS cells. Suitable fungal cells can include yeast cells, such as a *Saccharomyces cerevisiae* cells. Mammalian cells may, or may not, include human cells, and may or may not include embryonic cells.

Another aspect of the present invention provides a composition comprising an antibody or an antibody fragment according to the present invention. The composition may be a pharmaceutical composition and comprise a pharmaceutically acceptable carrier or excipient. Optionally, the only antibodies or antibody fragments present in the composition are those of the present invention. More preferably, there may be a single type of antibody or antibody fragment present in the composition, for example, wherein type is determined with respect to amino acid sequence, molecular weight and/or binding specificity to a citrullinated peptide. In this regard, the skilled person will appreciate that there may be some low levels of variation in the sequences of antibodies or antibody fragments in any population due, for example, to N-terminal variation and/or partial degradation; accordingly, in this context, a composition can be said to contain a single type of antibody or antibody fragment if, for example, at least about 80%, about 90%, about 95%, about 96%, about 97%, about 98%, about 99% or substantially 100% by weight of the detectable level of antibodies or antibody fragments in the composition are of a single type as determined with respect to amino acid sequence, molecular weight and/or binding specificity to citrullinated peptides.

In one aspect, the present invention provides an antibody or antibody fragment according to the present invention, or a composition according to the present invention for use in medicine, such as for use in a method of therapy, surgery or diagnosis that is performed on the human or animal body or on an ex vivo sample therefrom.

For example, in one aspect, the present invention provides an antibody or antibody fragment according to the present invention, or a composition according to the present invention, for use in the prevention, prophylaxis and/or treatment of mammals, including humans, against autoimmune disease, especially rheumatoid arthritis.

In other words, on one aspect, the present invention provides for the use of an antibody or antibody fragment according to the present invention, or a composition according to the present invention, in the manufacture of a medicament for the prevention, prophylaxis and/or treatment of mammals, including humans, against autoimmune disease, especially rheumatoid arthritis.

Also provided is a method for prevention, prophylaxis and/or treatment of a mammal, including a human, against autoimmune disease, especially rheumatoid arthritis, the method comprising the step of administering to the mammal an antibody or antibody fragment according to the present invention, or a composition according to the present invention.

In one aspect, the present invention provides a composition comprising the antibody or the antibody fragment, the polynucleotide, the vector and/or the cell of the present invention and a pharmaceutically acceptable carrier or excipient.

In one embodiment, the present invention provides the antibody or the antibody fragment, the composition, the polynucleotide, the vector and/or the cell for use in medicine.

In one embodiment, the present invention provides the antibody or the antibody fragment, the composition, the polynucleotide, the vector and/or the cell for use in the prevention, prophylaxis and/or treatment of mammals, including humans, against autoimmune diseases.

The autoimmune disease may be selected from the group consisting of rheumatoid arthritis, psoriatic arthritis, reactive arthritis and juvenile arthritis.

Also provided is the use of the antibody or the antibody fragment, the pharmaceutical composition, the polynucleotide, the vector and/or the cell for the manufacture of a medicament for use in the treatment of an autoimmune disease.

In another embodiment, the present invention provides a method of preventing and/or treating an autoimmune disease, the method comprising administering the antibody or the antibody fragment, the composition, the polynucleotide, the vector and/or the cell to a subject in need thereof.

In yet another embodiment, the present invention provides a method of reducing pro-inflammatory immune cells and/or increasing anti-inflammatory immune cells, the method comprising administering a therapeutically effective amount of the antibody or the antibody fragment, the composition, the polynucleotide, the vector and/or the cell to a subject in need thereof. The immune cells are selected from the group consisting of dendritic cells, macrophages and T cells.

The term "amount" of cells refers to for example the number of cells. In one aspect, the present invention provides a method for producing an antibody or an antibody fragment antigen-binding sequence according to the present invention comprising culturing one or more transformed host cells as described above, and recovering therefrom an antibody or an antibody fragment according to the present invention.

In one aspect, the present invention provides an in vitro method comprising culturing cells in the presence of the antibody or the antibody fragment according to the present invention.

In one aspect, the present invention provides a method of preparing a variant of the antibody or antibody fragments of the present invention, which variant retains the ability to bind to citrullinated peptides, the method comprising—
(i) providing a polynucelotide according to the present invention encoding a parent antibody or antibody fragment or polypeptide chain forming part thereof;
(ii) introducing one or more nucleotide mutations (optionally, up to 50, 40, 30, 20, 15, 10, 9, 8, 7, 6, 5, 4, 3, 2, or 1 nucleotide mutations), into the amino acid coding regions of the nucleic acid sequence, optionally within the regions encoding the VH and/or VL domain(s), such that the mutated nucleic acid encodes a variant antibody or antibody fragment having a different amino acid sequence compared to the parent antibody or antibody fragment;
(iii) expressing the variant antibody or antibody fragment, or polypeptide chain forming part thereof, that is encoded by the mutated polynucleotide; and
(iv) comparing the ability of the variant antibody or antibody fragment and the parent antibody or antibody fragment to bind to.

In one embodiment, nucleotide mutations may be introduced into the amino acid coding regions of the nucleic acid sequence randomly, or in a site-directed manner. Such mutations may result in the coding region encoding an amino acid sequence that contains one or more amino acid additions, one or more amino acid deletions and/or one or more amino acid substitutions compared to the amino acid sequence encoded by nucleic acid prior to mutation.

Such nucleotide mutations may, or may not, result in the coding region encoding an amino acid sequence that contains one or more variations in sequence in the antigen binding region. Such nucleotide mutations may, for example, result in amino acid sequence variation (that is, one or more amino acid additions, one or more amino acid deletions and/or one or more amino acid substitutions) present in, or exclusively in, the amino acid sequence that form one or more of the framework regions. Additionally, or alternatively, such nucleotide mutations may, for example, result in amino acid sequence variation (that is, one or more amino acid additions, one or more amino acid deletions and/or one or more amino acid substitutions) present in, or exclusively in, the amino acid sequence that form one or more of the complementarity determining regions. Levels of amino acid variations/modifications tolerated in respect of framework regions, CDRs and/or VH or VL domains as whole are discussed above in respect of the first aspect of the present invention and may be applied, mutatis *mutandis*, to the level of variation/modification that can be introduced according to the method of the eighth aspect of the present invention.

Additionally, or alternatively, such nucleotide mutations may, or may not, result in the coding region encoding an amino acid sequence that contains one or more variations in sequence in one or more parts of the antibody or antibody fragment other than the antigen binding region, such as in one or more of the CH1, CH2, CH3, CL regions or other regions.

Where one or more nucleotide mutations result in one or more amino acid substitutions in the encoded product, then the one or more substitutions may each, independently, be conservative or non-conservative substitutions. By "conservative substitutions" is intended combinations such as Gly, Ala; Val, Ile, Leu; Asp, Glu; Asn, Gln; Ser, Thr; Lys, Arg; and Phe, Tyr.

Nucleotide mutations may, for example, be introduced in order to render the sequence of the encoded antibody or antibody fragments closer to germline sequences, to improve the stability of the antibody or antibody fragment comprising the variant antigen binding region(s), to reduce the immunogenicity of the antibody or antibody fragment comprising the variant antigen binding region(s), and/or to avoid or reduce properties that could be disadvantageous in the manufacturing process. Such nucleotide mutations may be made using methods that are well known in the art.

In one embodiment of the present invention, the step of assessing the ability of the variant antibody or antibody fragment to bind to a citrullinated peptide may further comprise selecting those variants that have substantially equal or enhanced ability to bind to citrullinated peptides compared to the parent.

The ability of variants and parents to bind citrullinated peptides can be assessed by methods such as those discussed above.

In one embodiment, the method of preparing an antibody or antibody fragment according to the present invention, may optionally further comprise recovering a nucleic acid molecule that comprises the mutated nucleic acid sequence that encodes the variant antibody or antibody fragment, and optionally transforming a host cell with a composition comprising the recovered nucleic acid molecule and further optionally expressing the variant antibody or antibody fragment from the host cell, and yet further optionally recovering the thus-expressed variant antibody or antibody fragment from the host cell, and yet further optionally, formulating the recovered variant antibody or antibody fragment into a pharmaceutically acceptable composition.

In one aspect, the present invention also provides a variant antibody or antibody fragment obtained or obtainable by the method of the above aspect of the invention, or a pharmaceutically acceptable obtained or obtainable by the method of the above aspect of the invention, for use in medicine.

In one aspect, the present invention also provides a variant antibody or antibody fragment obtained or obtainable by the method of the above aspect of the invention, or a pharmaceutically acceptable obtained or obtainable by the method of the above aspect of the invention, for use in the prevention, prophylaxis and/or treatment of mammals, including humans, against autoimmune disease, especially rheumatoid arthritis.

In one aspect, the present invention also provides for the use of a variant antibody or antibody fragment obtained or obtainable by the method of the above aspect of the invention, or the use of a pharmaceutically acceptable obtained or obtainable by the method of the above aspect of the invention, in the manufacture of a medicament for the prevention, prophylaxis and/or treatment of mammals, including humans, against autoimmune disease, especially rheumatoid arthritis.

Accordingly, also provided by the present invention is a method for prevention, prophylaxis and/or treatment of a mammal, including a human, against autoimmune disease, especially rheumatoid arthritis the method comprising the step of administering to the mammal or subject a variant antibody or antibody fragment obtained or obtainable by the method of the above aspect of the invention, or the use of a pharmaceutically acceptable obtained or obtainable by the method of the above aspect of the invention.

Autoimmune Diseases

The term autoimmune diseases, is intended to include but is not limited to autoimmune diseases related to bone and joint, such as rheumatoid arthritis, psoriatic arthritis, reactive arthritis, juvenile arthritis, ankylosing spondylitis, Behcet's disease, Sjogren's syndrome, scleroderma, systemic lupus lupus erythematosus (SLE), polyarteritis nodosa; autoimmune diseases related to the respiratory tract such as sarcoidosis, vasculitis; autoimmune diseases related to cardiovascular system such as autoimmune myocarditis; autoimmune diseases related to the skin such as psoriasis, dermatitis herpetiformis, lichen planus, lichen sclerosus, pemphigus, sarcoidosis; autoimmune diseases related to the eyes such as autoimmune uveitis, autoimmune retinopathy; autoimmune diseases related to the gastrointestinal system such as, Crohn's disease, ulcerative colitis; autoimmune hepatitis; autoimmune diseases related to nervous system such as amyloidosis, multiple sclerosis, myastena gravis, and others such as Hashimoto's thyroiditis, Graves' disease, Addison's disease, diabetes mellitus, idiopathic thrombocytopaenic purpura, eosinophilic fascitis, antiphospholipid syndrome.

Amino Acid Sequence Identity

The percent identity between two amino acid sequences is determined as follows. First, an amino acid sequence is compared to, for example, SEQ ID NO:1 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information website at ncbi.nlm.nih.gov. Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt-j c:\seq2.txt -p blastp -o c:\output.txt. If the two compared sequences share homology, then the designated output file will present those regions of homology as aligned sequences. If the two compared sequences do not share homology, then the designated output file will not present aligned sequences. Once aligned, the number of matches is determined by counting the number of positions where an identical nucleotide or amino acid residue is presented in both sequences.

The percent identity is determined by dividing the number of matches by the length of the sequence set forth in an identified sequence followed by multiplying the resulting value by 100. For example, if a sequence is compared to the sequence set forth in SEQ ID NO:A (the length of the sequence set forth in SEQ ID NO: A being 10) and the number of matches is 9, then the sequence has a percent identity of 90% (i.e., 9÷ 10*100=90) to the sequence set forth in SEQ ID NO: A.

Antibodies

The term "antibody or antibody fragment" as referred to herein in the context of the present invention includes whole antibodies and any antigen binding fragment referred to as "antigen-binding region" or single chains thereof.

An "antibody" may refer to a protein comprising at least two heavy (H) chains and two light (L) chains inter-connected by disulfide bonds, or an antigen-binding portion thereof. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, CL.

The VH and VL regions can be further subdivided into regions of hypervariability, termed complementarity determining regions (CDR), interspersed with regions that are more conserved, termed framework regions (FR). Each VH typically comprises three CDRs and four FRs, arranged from amino-terminus to carboxy-terminus in the following order: FR1, CDR1, FR2, CDR2, FR3, CDR3, FR4. Likewise, each VL typically comprises three CDRs and four FRs, arranged from amino-terminus to carboxy-terminus in the following order: FR5, CDR4, FR6, CDR5, FR7, CDR6, FR8. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding region", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding region" of an antibody include—
(i) a Fab fragment, a monovalent fragment consisting of the VL, VH, CL and CH1 domains;
(ii) a F(ab')₂ fragment, a bivalent fragment comprising two Fab fragments linked by a disulfide bridge at the hinge region;
(iii) a Fab' fragment, which is essentially a Fab with part of the hinge region;
(iv) a Fd fragment consisting of the VH and CH1 domains;
(v) a Fv fragment consisting of the VL and VH domains of a single arm of an antibody,
(vi) a dAb fragment which consists of a VH domain;
(vii) an isolated complementarity determining region (CDR); and
(viii) a nanobody, a heavy chain variable region containing a single variable domain and two constant domains.

Furthermore, although the two domains of the Fv fragment, VL, and VH, are coded for by separate genes, they can be joined, using recombinant methods, by a synthetic linker that enables them to be made as a single protein chain in which the VL and VH regions pair to form monovalent molecules (known as single chain Fv (scFv)). Such single chain antibodies are also intended to be encompassed within the term "antigen-binding portion" of an antibody.

Diabodies consists of two polypeptides each comprising a heavy (VH) chain variable domain connected to a light chain variable domain (VL) on the same polypeptide chain (VH-VL) connected by a peptide linker. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a citrullinated peptide is substantially free of antibodies that specifically bind antigens other than citrullinated peptides). Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

Pharmaceutical Compositions

A pharmaceutical composition according to the invention may comprise a binding protein according to the invention in admixture with a pharmaceutically acceptable carrier and/or excipient, which will typically be selected with regard to the intended route of administration and standard pharmaceutical practice. The composition may be in the form of immediate-, delayed- or controlled-release applications. Preferably, the formulation is a unit dosage containing a daily dose or unit, daily sub-dose or an appropriate fraction thereof, of the active ingredient.

The pharmaceutical composition according to the invention may, or may not, be intended for, and, thus formulated in a manner suitable for, parenteral, intravenous, intra-arterial, intraperitoneal, intra-muscular, intra-cerebroventricular, or subcutaneous administration, or they may be administered by infusion techniques. They may be best used in the form of a sterile aqueous solution which may contain other substances, for example, enough salts or glucose to make the solution isotonic with blood or cerebral spinal fluid (CSF). The aqueous solutions may be suitably buffered (preferably to a pH of from 3 to 9), if necessary. The preparation of suitable pharmaceutical formulations under sterile conditions is readily accomplished by standard pharmaceutical techniques well-known to those skilled in the art.

Such formulations may include aqueous and non-aqueous sterile injection solutions which may contain anti-oxidants, buffers, bacteriostats and solutes which render the formulation isotonic with the blood or CSF of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

A therapeutically effective amount of an antibody or an antibody fragment according to the invention for administration to a patient, such as a human patient, on the basis of a daily dosage level may be from 0.01 to 1000 mg of antibody or antibody fragment per adult (for example, from about 0.001 to 20 mg per kg of the patient's body weight, such as 0.01 to 10 mg/kg, for example greater than 0.1 mg/kg and less than 20, 10, 5, 4, 3 or 2 mg/kg, such as about 1 mg/kg), administered in single or divided doses.

The physician, in any event, will determine the actual dosage which will be most suitable for any individual patient and it will vary with the age, weight, and response of the particular patient. The above dosages are exemplary of the average case. There can, of course, be individual instances where higher or lower dosage ranges are merited and such are within the scope of this invention.

EXAMPLES

Two monoclonal ACPAs isolated from RA patients have previously been described (van de Stadt et al., 2013).

Antibody assays. Anti-citrullinated fibrinogen (ACF) recombinant antibodies were detected with an ELISA as previously described (Raats et al., 2003). In short, IgG depleted fibrinogen was citrullinated using rabbit skeletal muscle PAD and coated on maxisorp microtitre plates. Supernatants were incubated 1:5 for one hour at room temperature on the coated plates and ACF antibodies were detected with horseradish peroxidase-conjugated mouse monoclonal anti-human IgG (HRP-IgG) and visualized with 3,3',5,5'tetramethyl benzidine (TMB).

Antibodies were tested for reactivity towards different citrullinated peptides as previously described (van de Stadt et al., 2011). In short, sera were incubated on streptavidin plates coated with biotinylated, citrullinated or native peptides. Bound antibodies were detected with HRP-IgG and then visualized with TMB. Reactivity was expressed as the difference in optical density (Δ OD) between citrullinated and native peptides.

Citrullinated fibrinogen peptide tetramers. Biotinylated citrullinated fibrinogen peptide NEEGFFSACitGHR-PLDKK (SEQ ID NO: 19) 0.5 mg/mL) was mixed with APC labelled streptavidin (0.5 mg/mL) in PBS/0.1% BSA and incubated on a roller bank overnight at 4° C. in the dark. Tetramers were purified over a bio-spin 30 column.

Isolation, proliferation, and identification of citrullinated fibrinogen specific single B-cells. For the isolation of B-cells, citrated blood was collected from an RA patient positive for aCCP. The study was approved by the local ethics committee.

Percoll gradients were used to isolate peripheral blood mononuclear cells (PBMC's) from the citrated blood. B-cells were isolated using anti-CD19 Dynabeads and DETACHaBEAD. Isolated B-cells were sorted for antigen-specificity by FACS sorting (BD FACSAria II) using anti-CD19-PerCP-Cy5 (BD Biosciences, San Jose, USA), anti-CD27-PE (BD Bioscience) and APC labeled fibrinogen peptide tetramers. Cells were seeded 1 cell per well in 96 well flat bottom plates and cultured in Iscove's modified Dulbecco's medium (IMDM) containing 10% FCS, 100 U/ml penicillin (Invitrogen), 100 μg/ml streptomycin (Invitrogen), 50 μM β-mercaptoethanol, 20 μg/ml human IgG depleted apo-transferrin 1 ng/ml IL-1β, 50 U/ml IL-2, 0.3 ng/ml TNFα, 0.5 μg/ml R848 in the presence of $1 \times 10^5$ irradiated (50Gy), CD40L-expressing EL4-B5 cells. After 14 days, supernatants were tested for ACF antibody production in an ELISA as described above.

Production of recombinant human antibodies. RNA was isolated from antigen-specific B-cells with Trizol according to the manufacturer's protocol. cDNA synthesis and RACE PCR were performed using the Clontech SMART cDNA synthesis kit. RACE PCR products for VL and VH were cloned into pGEM-t easy and sequenced with Big Dye Terminator according to the instructions provided by the manufacturers. VL and VH sequences followed by the constant domains of the human Kappa or Lambda and human IgG1 were ordered at Mr. Gene and cloned in pcDNA3.1 expression vectors. Expression vectors were used for transient transfection of HEK293F cells with 293fectin and OptiMEM, using the Freestyle HEK293F expression system.

Nucleotide sequence analysis. Nucleotide analysis was performed using the international immunogenetics information (IMGT) system.

Isolation and characterization of anti-citrullinated fibrinogen producing B cells. CD27+ B cells were enriched for cFib1; 0.2% of CD27$^+$ B cells were labeled with cFib1. Six hundred and seventy-two of these cells were seeded as a single cell per well and cultured for 14 days. Afterward, supernatants were harvested and screened for the presence of anti-citrullinated fibrinogen (ACF) antibodies by ELISA. Eight individual B-cell clones produced ACF antibodies. RNA was extracted from these clones and gamma-, kappa- or lambda-specific RACE PCR products were amplified and sequenced. Two of the antibodies were successfully expressed in Freestyle HEK293 cells by co-transfection of light and heavy chains, leading to the production of two recombinant IgG1 monoclonal antibodies: anti-cFib1.1 and anti-cFib1.2.

Citrullinated fibrinogen-specific B cells underwent extensive somatic hypermutation. Analyses of the VDJ genes showed that the VH of anti-cFib1.1 was formed by using V4-b*02, D2-15*01, and J5*02 in combination with 63 mutations leading to 29 amino acid substitutions. The VL (lambda) consisted of V1-51*01 and J1*01 in combination with 48 mutations leading to 28 amino acid substitutions. The VH of anti-cFib1.2 was formed by the combination of V1-02*02, D1-1*01, and J4*02 with 44 mutations resulting in 26 amino acid changes. The VL (kappa) of anti-cFib1.2 was based on V3-20*01 and J1*01 in combination with 21 mutations resulting in 13 amino acid substitutions. This shows that both monoclonal antibodies originated from different naive B cells and underwent extensive somatic hypermutation. Interestingly, both antibodies contain two N-glycosylation sites as a result of somatic hypermutation.

Recombinant anti-cFib1.1 and anti-cFib1.2 react with cFib1 but not aFib1 and are cross-reactive with other citrullinated peptides. The specificity of recombinant anti-cFib1.1 and anti-cFib1.2 was tested in an ELISA for the anti-cFib1 peptide. Both monoclonal antibodies were specifically directed against citrullinated cFib1 showing no reactivity with the aFib1 peptide. Both monoclonal antibodies were also tested for reactivity towards other citrullinated peptides derived from fibrinogen, enolase, and vimentin. Anti-cFib1.1 showed cross-reactivity towards cFib3 and to a lesser extent towards cEno, cFib2, and cVim. Anti-cFib1.2 showed cross-reactivity towards cEno and cFib2 and to a lesser extent towards cVim and cFib3. This shows that both monoclonal antibodies were citrulline specific and had distinct cross-reactivity patterns.

Example 1: Generation and Characterization of Monoclonal ACPAs

To characterize the binding profiles of ACPAs, we focused on several monoclonal ACPAs published so far (Amara et al., 2013; Uysal et al., 2009; van de Stadt et al., 2013; Ge et al., 2017).

Two monoclonal ACPAs isolated from RA patients have previously been described (van de Stadt et al., 2013) and it was showed that the N-linked glycans in the variable domains could modulate their binding profiles to citrullinated antigens (Rombouts et al., 2016). These two monoclonal ACPAs were designated E4 and F3 in the present study.

Each antibody was produced in two formats: as a chimeric non-glycosylated (NG) Ab, and as a chimeric glycosylated (WT) Ab, by genetically fusing the constant regions (CL and CH) of mouse IgG2b to variable regions (VL and VH) of human E4 or F3. The antibodies were expressed in HEK293 cells by transient transfection and purified by affinity chromatography. The comparable Fc glycosylation pattern between E4 and F3 was observed by mass spectrometry (MS) (FIG. 8, Table 1).

TABLE 1

Relative glycan distributions (%) of E4 and F3.

| Glycan composition | Suggested structure | F3 | E4 |
|---|---|---|---|
| HexNAc2Hex4 | M4 | — | 0.1 ± 0.1% |
| HexNAc2Hex5 | M5 | 0.2 ± 0.02% | 0.9 ± 0.1% |
| HexNAc3Hex3 | A1 | 0.2 ± 0.004% | 0.2 ± 0.03% |
| HexNAc4Hex3 | A2 | 0.2 ± 0.01% | 1.0 ± 0.7% |
| HexNAc4Hex4 | A2G1 | 0.1 ± 0.04% | 0.1 ± 0.1% |
| HexNAc4Hex5 | A2G2 | — | 0.1 ± 0.04% |
| HexNAc4Hex6 | A2G3 | 0.1 ± 0.04% | — |
| HexNAc5Hex3 | A2B | 0.2 ± 0.04% | — |
| HexNAc5Hex4 | A2BG1 | — | 0.8 ± 0.8% |
| dHexHexNAc3Hex3 | FA1 | 9 ± 1% | 11 ± 1% |

TABLE 1-continued

Relative glycan distributions (%) of E4 and F3.

| Glycan composition | Suggested structure | F3 | E4 |
|---|---|---|---|
| dHexHexNAc3Hex4 | FA1G1 | 1 ± 0.1% | 2 ± 0.2% |
| dHexHexNAc3Hex4NeuAc | FA1G1S1 | 0.1 ± 0.02% | — |
| dHexHexNAc4Hex3 | FA2 | 74 ± 2% | 67 ± 2% |
| dHexHexNAc4Hex4 | FA2G1 | 14 ± 1% | 16 ± 1% |
| dHexHexNAc4Hex5 | FA2G2 | 0.7 ± 0.1% | 1.1 ± 0.2% |
| dHexHexNAc4Hex4NeuAc | FA2G1S1 | 0.1 ± 0.02% | — |
| dHexHexNAc5Hex3 | FA2B | 0.4 ± 0.04% | 0.3 ± 0.1% |
| dHexHexNAc5Hex4 | FA2BG1 | 0.2 ± 0.03% | — |
| dHexHexNAc4Hex4NeuAc | FA2G1S1 | — | 0.1 ± 0.04% |

Glycan composition and suggested glycan structures are given as well as the relative glycan distributions of F3 and E4. Values are given according to the mean and standard deviation of three digested trypsin sample replicates.

For comparison, we also analyzed two previously reported monoclonal ACPAs designated D10 and B2. They were generated from joint-derived B cells of RA patients and produced in the same mouse IgG2b-based chimeric format (Amara et al., 2013). In addition, two ACPAs (ACC1 and ACC4) that were previously shown to be arthritogenic and cross-reactive with joint type II collagen (Ge et al., 2017; Uysal et al., 2009) were analyzed.

Figure 1A:
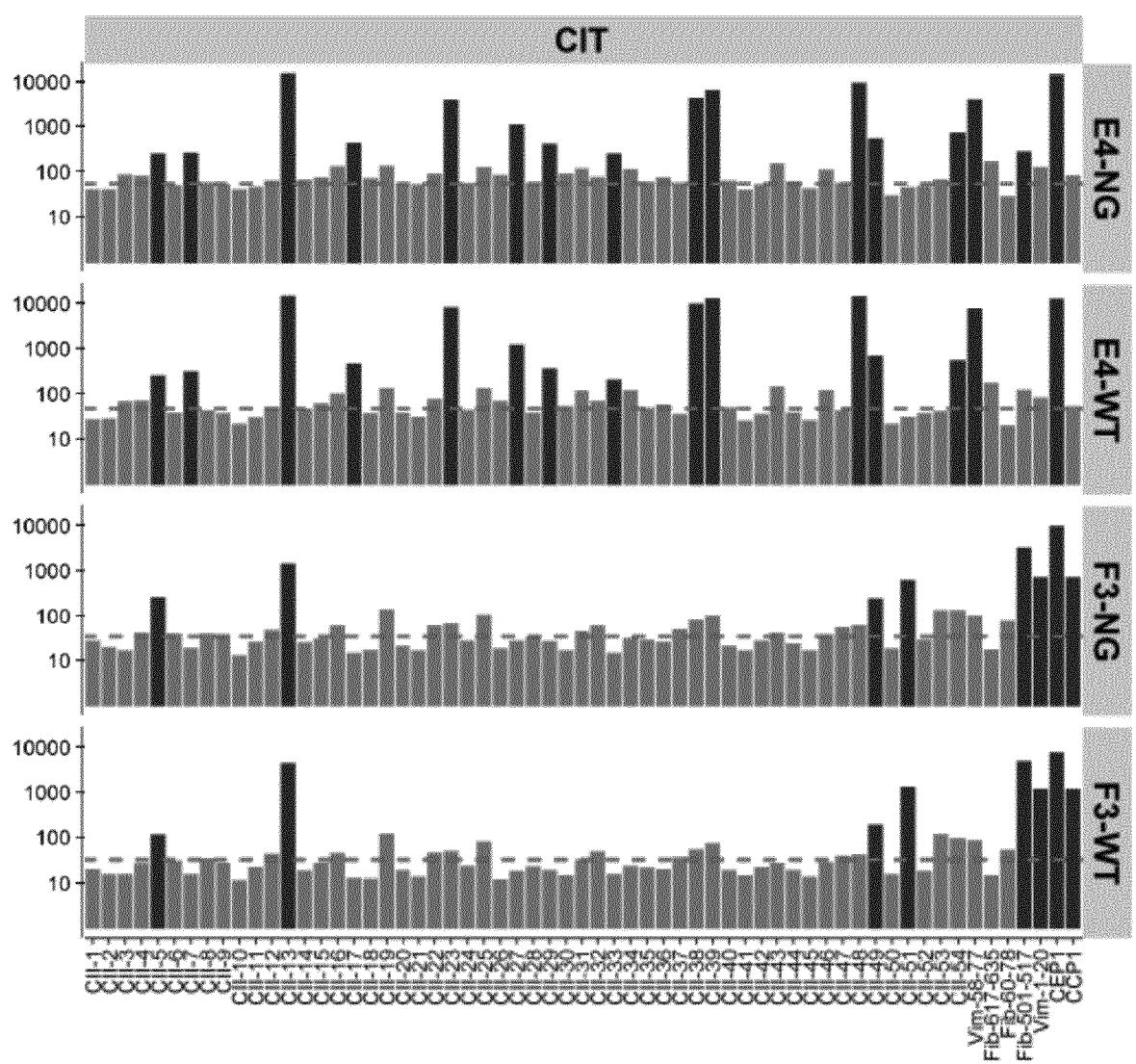
FIGS. 1A and 1B. Reactivity of Cyclic 17-mer citrullinated CII peptides against antibodies E4 and F3.
Figure 1B:
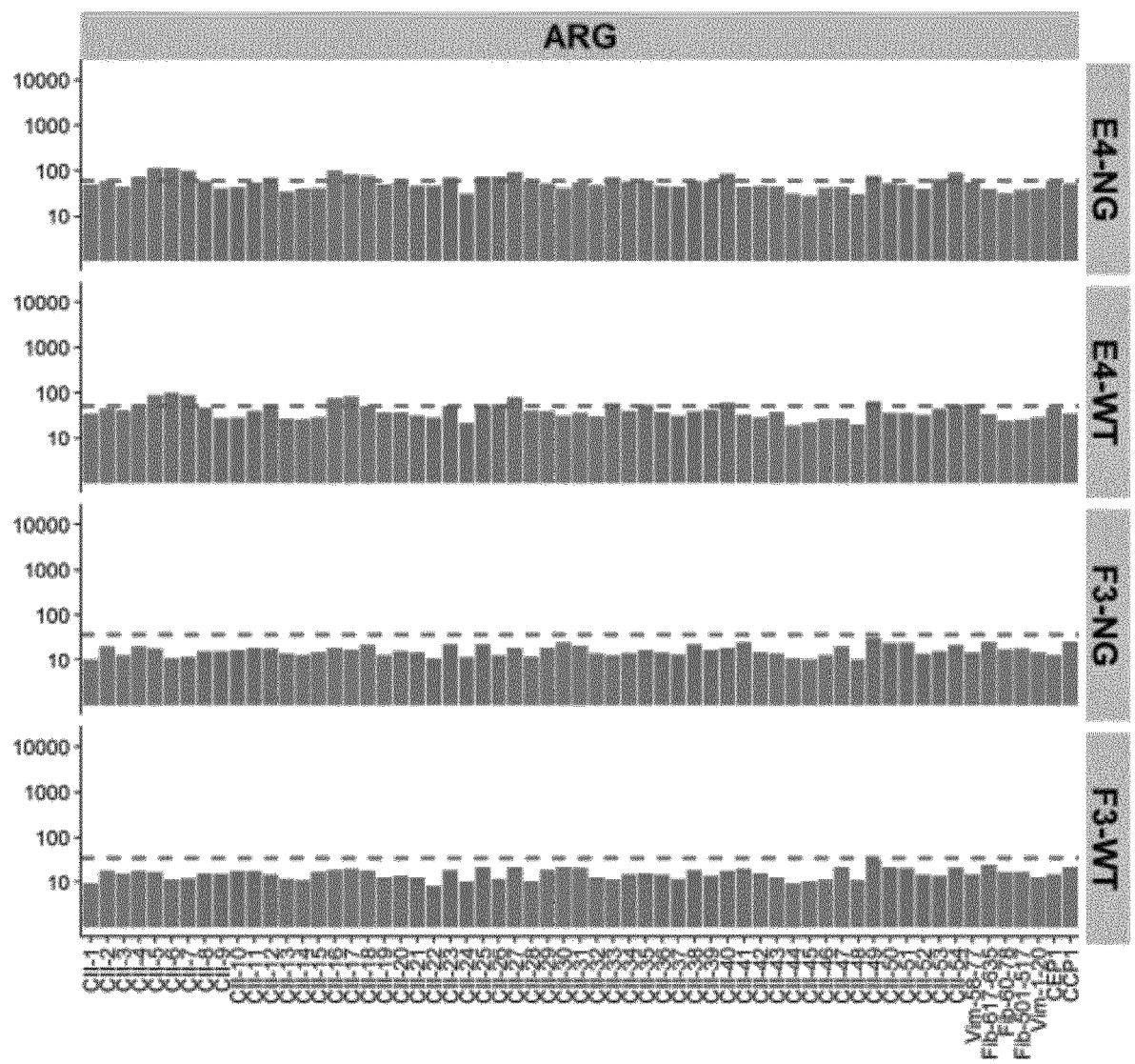

To comprehensively map the breadth of reactivity of chimeric E4 and F3, a large set of 17-mer cyclic CII peptides centered around either an arginine or a citrulline residue were designed and examined by Luminex immunoassay. Some well-characterized citrullinated (Cit) peptides derived from α-enolase (CEP1), fibrinogen, vimentin, and filaggrin (CCP1) were also included (Burska et al., 2014). A remarkable reactivity difference was observed between Cit-peptides and respective arginine (Arg)-containing peptides (FIGS. 1A and 1B). Neither E4 nor F3 showed reactivity towards any Arg-peptides. However, both E4 and F3 recognized several citrullinated CII peptides (CII-C-13, CII-C-23, CII-C-38, CII-C-39, and CII-C-48) and CEP1. The CII peptides CII-C-17, CII-C-27, CII-C-29, CII-C-49, and CII-C-54 and Vim_58-77 were only recognized by E4, while the peptides CCP1, Vim_1-20, and CII-C-51 were solely bound by F3, suggesting qualitative differences in cross-reactivity between E4 and F3. Notably, all the CII-derived peptides recognized by both ACPAs contain a conserved "Cit-Gly" motif in their sequences. Subtle differences in binding strength/affinity were observed between WT- and NG-forms of the two monoclonal antibodies (mAbs), which is in good agreement with a previous observation (Rombouts et al., 2016). In contrast, no binding of the other two monoclonal ACPAs (D10 and B2) to any constituent of the present peptide library was observed (data not shown). Furthermore, we measured the affinity of both E4 and F3 for CEP1 by surface plasma resonance (SPR) using the corresponding arginine control peptide as a reference and found that E4 showed stronger affinity/avidity than F3 (FIGS. 3A-C). Both D10 and B2 (FIG. 3E-F) showed weak binding to CEP1 in our SPR assay with empty reference channel, but the specificity for CEP1 was totally abrogated when using its arginine-containing control peptide as a reference channel, showing that neither D10 nor B2 is a citrulline-specific antibody.

Materials and Methods

Expression and purification of chimeric antibodies. Chimeric antibodies containing a human variable region and a mouse constant region were designed. The mouse IgG2b constant region sequence was obtained from UniProtKB with accession number P01867, whereas the mouse lambda-1 was from UniProtKB entry P01843. First, vectors containing the mouse IgG2b heavy chain (HC) constant region and the lambda light chain (LC) constant region, were created. The variable regions of HC and LC from RA patients were then inserted in the frame before the mouse constant region. To do so, four DNA fragments were synthesized at Eurofins with restriction sites at the 5' and 3' ends: 1) the mIgG2b constant region with restriction sites NheI and BamHI, 2) the lambda constant region with HindIII and BamHI, 3) the HC variable region with KpnI and NheI, and 4) the LC variable region with KpnI and HindIII. The synthesized genes for the constant regions of both HC and LC were digested using FastDigest™ restriction enzymes. The digested DNA fragments were cloned into the mammalian expression vector pCEP4 that was digested using the same restriction enzymes. After ligation, two vectors containing mouse IgG2b and Lambda constant regions were obtained, designated pCEP4-mIgG2b and pCEP4-mL, respectively. The synthesized human variable regions were also digested using FastDigest™ restriction enzymes and cloned into pCEP4-mIgG2b and pCEP4-mL digested with the same restriction enzymes. After ligation, plasmid propagation and sequence verification, plasmids containing HC and LC were co-transfected into Expi293F™ cells with FectoPRO™ DNA transfection reagent. The supernatants were harvested 6 days post-transfection. The chimeric antibody was purified using a 5 mL HiTrap Protein G HP affinity column. The purified antibodies were dialyzed against PBS and the endotoxin was determined using Pierce™ LAL Chromogenic Endotoxin Quantitation Kit.

Surface plasmon resonance analysis. Binding of peptides to the given antibody was analyzed by SPR using a Biacore 2000 biosensor at 25° C. Briefly, the biotin-conjugated peptide was coupled to an SM sensor chip by streptavidin binding. Then the Fab fragment or full-length antibody was diluted in PBS-P running buffer (20 mM phosphate buffer, 2.7 mM KCl, 137 mM NaCl and 0.05% Surfactant P20) and injected at in a series of concentrations. Data processing and analysis were performed using Biacore 2000 evaluation software.

Preparation and purification of the chimeric E4$_{Fab}$ fragment. The E4$_{Fab}$ fragment was prepared using the ImmunoPure Fab Preparation Kit. The Fab fragments for D10 and B10 were produced as described previously (Amara, K. et al. *Monoclonal IgG antibodies generated from joint-derived B cells of RA patients have a strong bias toward citrullinated autoantigen recognition*, J Exp Med 210(3), 445-55, 2013). Papain cleavage was evaluated by sodium dodecyl sulfate (SDS) polyacrylamide gel electrophoresis. The Fab fragments used for crystallization were further purified by size exclusion chromatography using a HiLoad 16/600 Superdex 200 column. Aliquots of purified E4$_{Fab}$ fragments in 20 mM Tris pH 7.4, 50 mM NaCl were mixed with the cognate peptides in 2-3 times molar excess and incubated overnight before setup of crystallization screens or storage at −80° C. before further use.

Peptide design and synthesis. A library of 17-mer cyclic peptides derived from human collagen was synthesized by WuXi Apptech. In each peptide, the arginine (or the citrulline) residue of interest is flanked by 7 neighboring residues on both sides, then capped by a Cys residue at each terminus to form the cyclic conformation. Biotin was added to the very N-terminus of the peptide via the flexible linker aminohexanoic acid (Ahx).

Conclusion: E4 showed a broader range of reactivity than F3 towards citrullinated CII peptides, but the N-glycan in the antibody combining site did not affect the specificity.

Although they share the same Fc domains (the subtype of IgG2b) and Fc-glycosylation pattern, the differences observed in our experiments imply that the fine specificities of E4 and F3 also play important roles in governing their functions. In comparison, the two ACPAs ACC1 and ACC4 were consistently pathogenic.

Example 2: E4 Protects Against Collagen Antibody-Induced Arthritis (CAIA)

Figure 2:
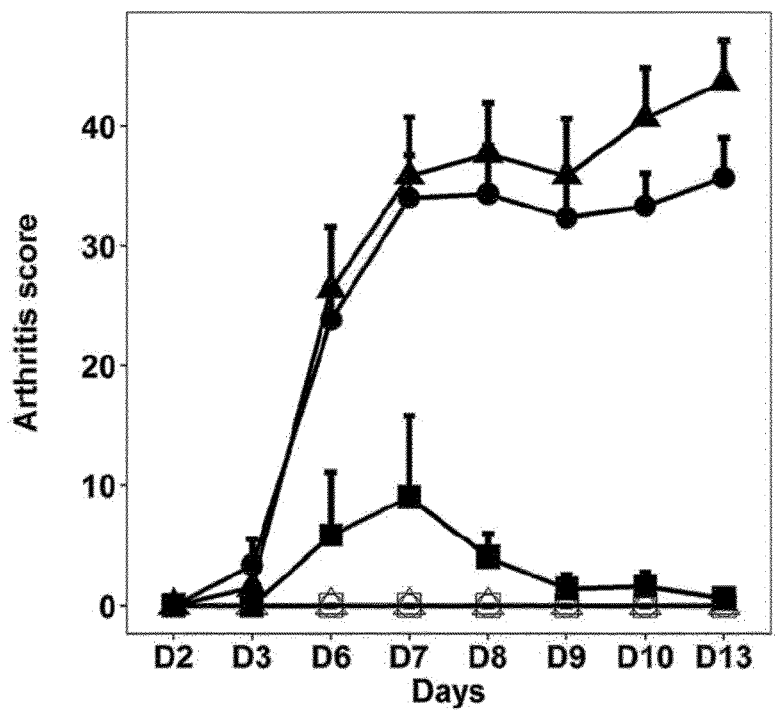
FIG. 2. Protective effect of chimeric E4NG in the CAIA model. Experimental animals
(Cia9i, which is a B10.Q strain with a chromosomal fragment inherited from the NOD mouse containing the fcgr2b and the fcgr3 genes. The mouse strain is slightly more susceptible to arthritis but otherwise largely a C57Bl strain) were injected with 6 mg of Abs (either single Ab or mixture of Abs as indicated) on day 0 and LPS was given on Day 3 for boosting the disease. CAIA severity and incidence were evaluated until Day 13.
(A) Mean arthritis score in CIA9i (n=5 or 6) mice. Data are presented as mean±SE and include both arthritic and healthy animals.
(B) CAIA incidence in CIA9i mice. Data represent CAIA assessment.
-○—chimeric E4NG(3 mg)+M2139(3 mg), -Δ—chimeric E4NG(3 mg)+M2139(6 mg),
-■—M2139(3 mg)+M2139mut(3 mg), -●—ACC1(3 mg)+M2139(3 mg),
-▲—ACC1(3 mg)+M2139(6 mg),
(C) Histological scores of H&E staining and TRAP stained joint tissue in groups of mice injected with different Abs (n=4-6 per group).
Figure 2:
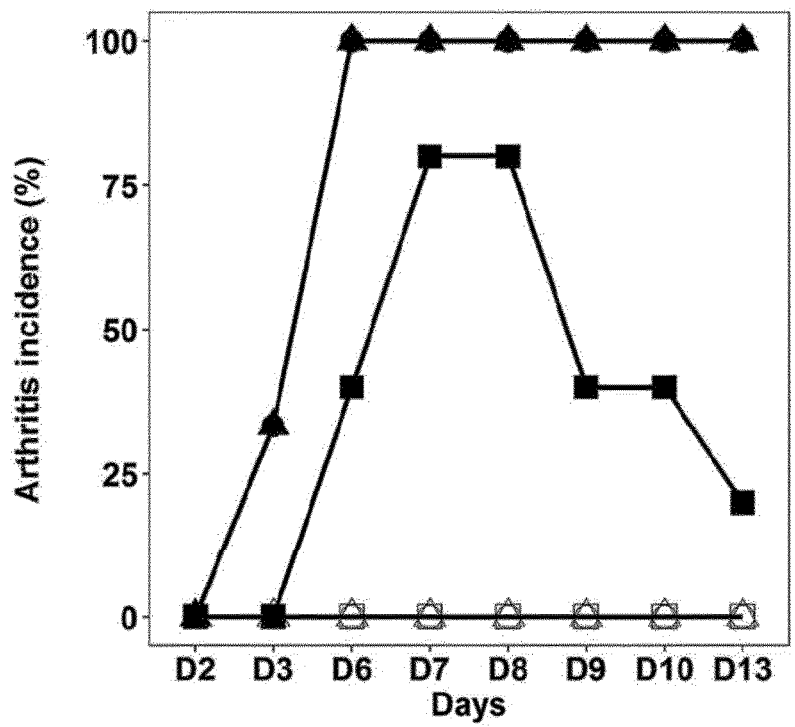
Figure 2:
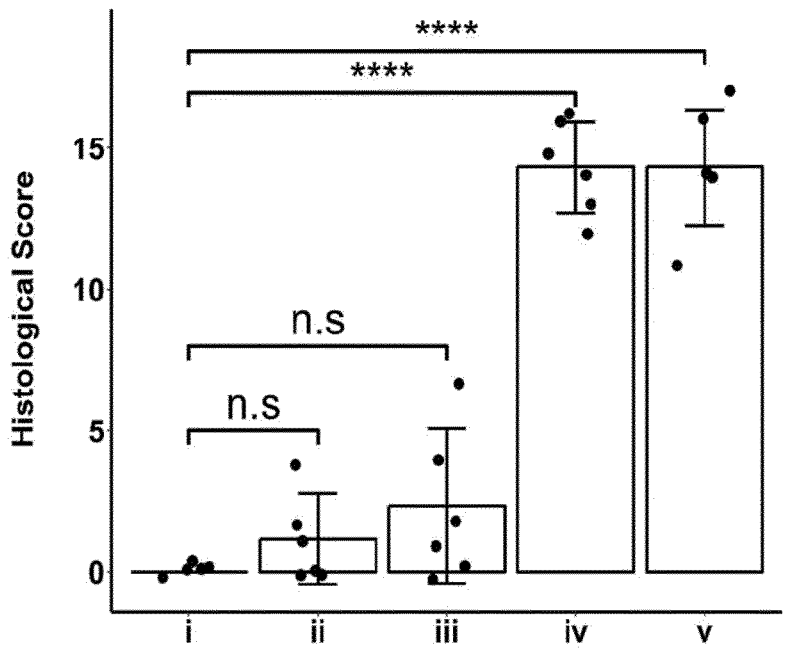
Figure 2:
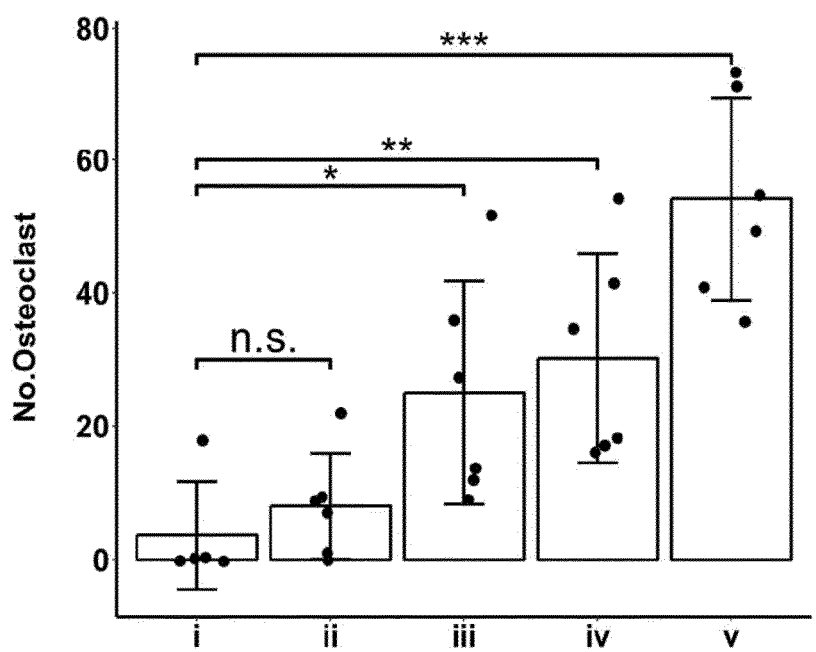
Figure 2:
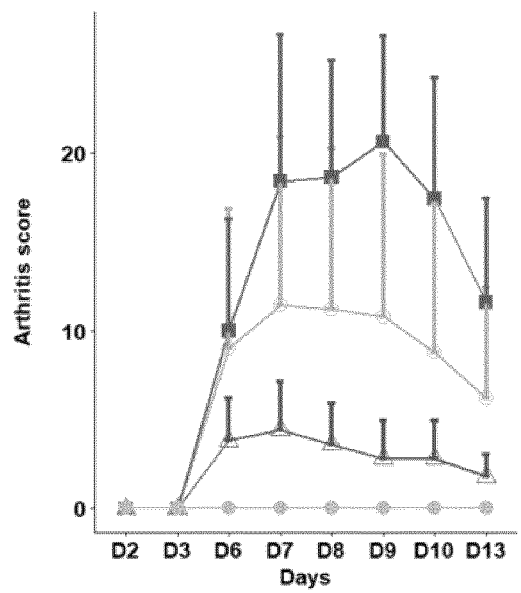
Figure 2:
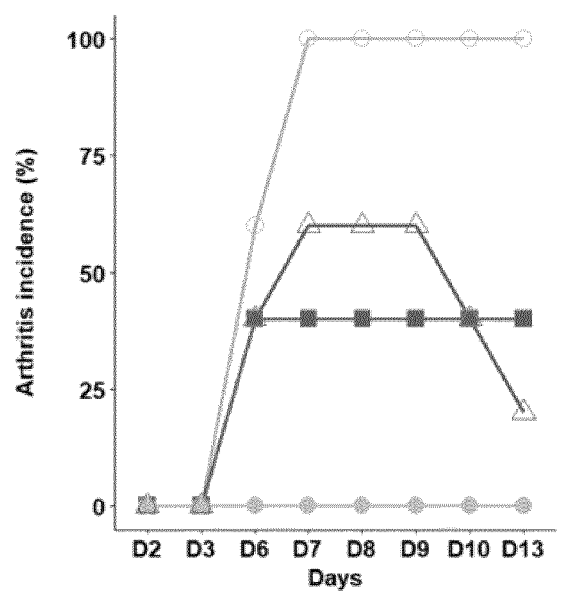

To evaluate the function of citrulline-specific ACPAs, they were injected intravenously into mice. In agreement with a previous report showing that ACC1 is pathogenic (Uysal et al., 2009), a combination of ACC1 with M2139 induced severe arthritis (FIG. 2A-B). Histopathologic examinations of joints confirmed that the groups of mice administrated with ACC1 and M2139 had severe synovitis, joint inflammation, and histological damage. In contrast, the groups of mice injected with E4 and M2139 did not show any clinical symptoms of arthritis, while a mild disease was induced in the group of mice by M2139 and its mutant M2139 (M2139mut) (FIG. 2A-B). To further investigate the bone erosion in mice, the osteoclast staining by TRAP (reflecting bone-resorbing activity) was performed (FIG. 2C). As expected, the number of osteoclasts is significantly increased in the groups of mice injected with M2139 or M2139 combined with ACC1, while there was no difference between the naïve group and the group injected with 3 mg of E4 confirming the protective effects of E4 in this disease model (FIG. 2D). However, mild joint bone erosion in the mouse injected with a higher dose of E4 (6 mg) was also observed, possibly resulting from immune complex engagement of cell surface molecules, leading to osteoclast-mediated bone destruction. In contrast, the F3 antibody in combination with M2139 did not show any protective effects in the animal experiments (FIG. 4A-B). It has been reported that ACPAs selected from phage display libraries derived from RA patients, could have a similar potent suppression of experimental arthritis (Chirivi et al., 2013). The causative mechanism was shown to be related to an inhibition of neutrophil extracellular traps (NETs) formation as these antibodies were specific for a citrullinated peptide derived from the N-terminus of histone 2A. Importantly, only F3 but not E4 interacted with this peptide (FIG. 3F-G). The suppressive effect of E4 was also apparent in Ncf1 mutated mice (Table. 2) that are unable to form NETs (Schauer et al., 2014).

TABLE 2

Suppressive effects of E4 antibody in anti-CII antibody-induced arthritis

| Group | Incidence | Max arthritis score (mean ± SEM) |
|---|---|---|
| M2139 + mM2139 | 3/5 | 3.4 ± 1.7 |
| M2139 + E4 | 0/5 | 0.0 ± 0.0 |

Groups of 19-20 months old male B10RIII.Ncf1$^{m1j/m1j}$ mice (n = 5 for each group) were injected i.v. with 6 mg of M2139 or 6 mg of M2139 in combination with either 3 mg of mM2139 or 3 mg of E4. 25 μg of LPS per mouse was given i.p. on day 5 to boost the incidence and severity of arthritis.

Materials and Methods

Animals. For the study of collagen antibody-induced arthritis (CAIA), 4 months old Cia9i mice or 19-20 months old B10RIII.Ncf1$^{m1j/m1j}$ mice (Khmaladze et al., 2014) were used.

Collagen antibody-induced arthritis. Five groups of Cia9i mice and two groups of B10RIII.Ncf1$^{m1j/m1j}$ mice were injected with the given antibodies. All mice received 25 μg of lipopolysaccharide (LPS) from *Escherichia coli* intraperitoneally on day 3. The development of arthritis was monitored daily for a period of 13 days using an extended scoring protocol. The clinical arthritis was evaluated as described previously (Nandakumar, K. S. et al. *Collagen type II-specific monoclonal antibody-induced arthritis in mice: description of the disease and the influence of age, sex, and genes*. Am J Pathol 163(5), 1827-37, 2003).

Conclusion: Some ACPAs (such as E4) protect mice from developing experimental arthritis through a unique pathway. Other ACPAs (such as F3) did not have any apparent impact, whereas ACPAs cross-reacting with cartilage or cartilage fragments in the synovia, such as ACC1 and ACC4, mediate arthritis. The results thus demonstrate that E4 has a protective rather than pathogenic effect in an experimental model of RA.

Example 3: Cellular Targets of E4

We reasoned that the protective effect of E4 might be due to engagement with cell surface proteins and subsequent activation of anti-inflammatory pathways in certain cell types. Therefore, we determined the binding profiles of E4 using flow cytometric analysis. E4 was found to primarily bind to subgroups of CD11c$^+$ and CD11b$^+$ cells in both naïve and arthritic mice, but not to neutrophils or T cells (FIG. 5A-B). Moreover, it showed no staining of naïve mouse cartilage but gave considerable staining of inflamed synovial tissue adjacent to cartilage in CAIA mice. This suggests enhanced generation of citrullinated antigens adjacent to damaged cartilage regions in arthritic mice. In comparison, the M2139 antibody did not show any staining of certain cell types but strong binding of mouse joint cartilage. In addition, E4 injections in mice lead to decrease of CD11b/c+ MHC class II+dendritic cells (FIGS. 5C-D) and increase of CD11b/c+F4/80+ macrophages (FIG. 5E). E4 could thus play a role in activating anti-inflammatory macrophages thereby exhibiting a therapeutic effect in RA.

Given the observed positive staining of E4 in inflammatory regions of damaged mouse cartilage, we reasoned that E4 might also recognize antigens in organs potentially affected by RA, and performed immunohistochemical staining of lung tissue. Interestingly, a positive staining of E4 was observed in the lungs of both a naïve mouse and a mouse challenged with a high dose of mannan. This directly demonstrated the omnipresence of citrullinated antigens in normal as well as in inflamed lungs. Similarly, the highly pathogenic ACC1 also showed positive staining, corroborating its reactivity to citrullinated peptides (Ge et al., 2017). In contrast, there was no detectable staining for antibodies M2139 or ACC4.

Next, immunohistochemical staining of a central lymphoid organ, i.e. thymus—murine as well as human, to analyze whether potential targets are present, were performed. Surprisingly, E4 showed positive staining in both human and mouse thymus (data not shown). In contrast, M2139 stained a few medullary thymic epithelial cells whereas ACC4 was negative in all experiments. Furthermore, a double staining of thymus tissue by both E4 and CD11c was positive, confirming that E4 bound to CD11c$^+$ cells, presumably a subset of migratory thymic dendritic cells. This is in good agreement with the observation of positive staining of E4 on splenic CD11c$^+$ cells as demonstrated by a FACS assay. An immuno-precipitation experiment showed that E4 bound many proteins extracted from spleen, lymph node, lung, and thymus (FIG. 6).

Materials and Methods

Flow cytometry. Groups of three Cia9i mice each were i.v. injected either with 1 mg of biotinylated E4 antibody or with 2 mg of biotinylated M2139 antibody. The control group received PBS instead. 24 h later the mice were sacrificed; single-cell suspensions from spleens were obtained and analyzed by flow cytometry. Flow cytometric analysis was performed using combinations of fluorochrome-conjugated monoclonal antibodies to mouse CD4, CD8, CD11c, CD11 b, Ly6G and APC-conjugated streptavidin. A SORP BD LSR II analytic flow cytometer was used for acquisition, and the data were analyzed with FlowJo software. Streptavidin—APC—positive cells considered as antibody-bound cells.

Histology. For histological assessment, knee joints and paws from adult mice were dissected, decalcified, dehydrated, and paraffin-embedded as previously described. Sections were stained with hematoxylin/eosin or toluidine blue. For determination of mAb reactivity with joint tissue in vivo, 2-days old neonate Cia9i mice were intraperitoneally injected with 100 μg of biotinylated mAbs. After 48 hours, the knee joints were snap frozen in isopentane on dry ice and stored at −80° C. Joint sections were fixed in 4% paraformaldehyde for 5 min, rinsed in PBS, blocked for endogenous peroxidase for 30 min (0.5% $H_2O$ with 0.1% Tween 20), incubated with Extravidin® peroxidase for 30 min, and developed with diaminobenzidine. To assess direct binding of mAb to the tissue sections (cartilage, lung, and thymus) in vitro, limbs from 2 days old naïve Cia9i neonates were harvested, snap frozen and cryosectioned. Sections were subjected to biotinylated mAb for 40 minutes. Extravidin® peroxidase and DAB were used for detection.

Immunohistochemistry of human and murine tissues. Human thymic tissue was obtained from children undergoing corrective cardiac surgery at Sahlgrenska University Hospital, Gothenburg, Sweden. Human and murine thymus tissue embedded in OCT compound was ixed with cold acetone and blocked with Protein Block. The human and the naïve murine samples were stained with ACC1, ACC4, E4NG and M2139. The tissues were stained with Streptavidin Alexa Fluor 555 and Hoechst. The murine samples pre-injected with the given antibodies were only stained with streptavidin and Hoechst as described in the previous step. Sections were mounted with ProLong Gold Antifade Mountant and images were acquired using an LSM700.

Conclusion: Overall, these data clearly indicate that citrullinated antigens are abundantly present, not only in the lung but also in the thymus. In addition, this study is the first to demonstrate the protective effect of ACPA in experimental arthritis and that citrullinated antigen are present also in CD11c+ cells in the thymus, suggesting that dendritic cells (DC) may participate in the central tolerance for citrullinated antigens.

E4 predominantly bound to CD11b+/CD11c+ cells, indicating that it interacts with the macrophage-dendritic type of cells. This may still affect many different cellular functions. It is possible that E4, by targeting CD11b/c+ macrophages and DCs, diminishes their immunogenicity, contributing to the restoration of self-tolerance in the CAIA model.

Example 4

Overall Structure of E4NG Fab and Complex Forms. To identify the structural determinants of citrulline-specificity and epitope cross-reactivity of the E4, we determined the crystal structures of its Fab fragments complexed with three distinct citrullinated peptides (CII-C-13, CII-C-48, CEP1), and for comparison also in unbound state (FIG. 9A). Peptides CII-C-13 ($^1$CPAGEEGKXGARGEPGCA$^{18}$, X=citrulline) and CII-C-48 ($^1$CEAGEPGEXGLKG-HRGCA$^{18}$) are derived from CII, whereas CEP1 ($^1$CKIHAXEIFDSXGNPTVECK$^{20}$) is a well-characterized peptide originating from α-enolase. The Fab fragment in the complexes with CII-C-13 and CEP1 contains murine IgG2σ constant region, whereas the E4$_{Fab}$ fragment present in the crystals of the unbound state and complex with CII-C-48 contains the murine IgG2b constant region. This results in significant difference in the relative orientations of the variable and the constant domains of the single E4$_{Fab}$ per asymmetric unit in these crystals. Pairwise superposition of the individual (identical) constant and variable domains of all four structures results in RMSDs of 0.2-1.0 Å, indicating high backbone conformational similarity.

Molecular Determinants of Citrulline Recognition and Cross-reactivity. The antigen-binding paratope is formed by the heavy (H) and light (L) chain variable with largest contributions from H3 and L1 (FIG. 9B). It consists of two narrow grooves that are connected at both ends and in the middle separated by a ridge formed by H-G102 and H-S103 from CDR H3 and L-F33 of CDR L1, thus giving it an overall ring- or zero-like shape. At one end of the "zero" the groove has a distinctly negative electrostatic potential, whereas the dominating features at the other end are a 8 Å deep pocket formed by H2 (H-W48, -S51, -Y59), H3 (H-I99, -N105) and L3 (L-F99) residues, flanked by a hydrophobic patch and a patch of positive electrostatic potential. All three distinct peptide epitopes adopt a bend conformation to match the groove. However, they show identical conformations only for the signature Cit-G motif, the directly following residue as well as three preceding amino acids, with the long polar citrulline side chain being inserted into the deep pocket. Citrulline recognition is largely mediated by the formation of three hydrogen bonds to its side chain, namely between the oxygen atom of the ureido moiety and the hydroxyl group H-S51 as well as the amine nitrogen of H-W48, and between one of the ureido group nitrogen atoms and the carboxamide oxygen of H-N105. Since this deep pocket is partly non-.polar, insertion of a charged side chain should be energetically disfavored, explaining the strict selectivity for citrulline as compared to arginine-containing epitopes. Additionally, three direct and two water-mediated hydrogen bonds were found to be conserved in all three E4$_{Fab}$-peptide complexes: the citrulline interacts with the hydroxyl group of H-Y59, the Cit-G motif glycine and the peptide residue preceding the citrulline, p(Cit-1), interacts with the backbone oxygen and nitrogen of H-G102, respectively, and the p(CIt-3) residue makes water-mediated contacts to backbone groups of H-S32 and H-G101, respectively.

Several additional polar contacts are only partially conserved, namely the hydrogen bonding of the Cit-G motif glycine to the carboxamide group of H-N105 (direct) and the backbone oxygen of H-S103 (water-mediated) observed in the E4$_{Fasb}$-complexes with CII-C-48, and the water-mediated hydrogen bonds between the p(Cit-2) and the hydroxyl groups of H-T55 and H-T57 observed in the CII-C-13- and CEP1-complexes.

All these fully or partially conserved polar interactions engage peptide main chain atoms and are therefore not epitope-sequence specific, giving rise to the strong cross-.reactivity of E4. From the three epitopes analyzed here, the entire CEP1 sequence, except for pE7 and pI8, is well defined in electron density. For CII-C-13 and CII-C-48, the electron density is observed only for residues 4-13 and 5-13, respectively.

The interactions between the mE4 paratope and the peptide antigen are dominated by polar contacts, as relatively few short distance hydrophobic contacts (<3.8 Å) were observed in all three complexes. the primary polar nature of the mE4 paratope, providing numerous hydrogen bond donor and acceptor groups, is further highlighted by the observation of three glycerol molecules originating from the crystallization/cryoprotection solution in then peptide binding groove of the antigen-free $mE4_{Fab}$ crystal structure.

Superposition of the $mE4_{Fab}$-peptide complex variable domains revealed that the conformation of the CDR loops is almost identical despite their binding to different peptide sequences. Superposition with the corresponding peptide-free structure revealed that the paratope is stably preformed in absence of antigen as peptide binding induced few and very modest changes in CDR residue conformations.

Structural comparisons with other ACPAs. The crystal structures of two murine ACPAs, ACC1 (PDB accession code: 5mu0) and ACC4 (PDB accession code: 2w65) in complex with citrullinated peptide, have been reported previously (Winter et al., 2013. Decision making in xia2.Acta Crystallogr D Biol Crystallogr; 69(Pt 7):1260-73; R: A language and environment for statistical computing [program]. Vienna, Austria: R Foundation for Statistical Computing, 2017). ACC1 is a highly arthritogenic antibody that targets citrullinated C1 epitope and CII but also cross-reacts with several non-citrullinated epitopes on native Oils as well as with some classical citrullinated peptides like CCP2 and CCP1. ACC4 is on the other hand highly specific for the citrullinated CII-C1 epitope but only in the non-native, single α-chain form. Interestingly, it enhanced arthritis severity when given concomitantly with another CII-specific antibody (M2139). We also determined the crystal structures of the human ACPAs B2 and D10 antibodies that were the first to be cloned from human RA. Both B2 and D10 were co-crystallized with full-length or truncated versions of CEP-1, but no electron density attributable to bound peptides was observed.

Superposition of the $E4_{Fab}$, $ACC1_{Fab}$, $ACC4_{Fab}$, $B2_{Fab}$, and $D10_{Fab}$ structures revealed significant differences in the size, shape, and properties of their paratopes. The ACC1 paratope is set apart from the others by being in a deep, open-ended cleft between the heavy and the light chain CDR that enables it to bind to a single α-chain of the CII epitope most likely bulging out of a rigid triple-helical collagen structure. Citrulline versus arginine specificity is most likely imposed by the electrostatic properties of a nearby surface patch. In contrast, the ACC4 paratopes in a smaller, enclosed groove and the citrulline specificity is mediated by a network of hydrogen bonds to the ureido moiety.

Since no peptide complex structures of $B2_{Fab}$ and $D10_{Fab}$ are available, and the peptide specificities are unknown, the precise location of their paratopes and detailed features of the peptide recognition could not be determined.

Based on the small number of available crystal structures of ACPAs in complex with citrullinated epitopes, we can conclude that citrulline specificity may be achieved by providing either both a hydrogen-bonding partner group pattern selective for citrulline and electrostatic surface properties that bias against arginine, or just the latter feature, but that no conserved feature regarding the shape of the citrulline binding pocket can be expected.

Materials and Methods

Mass spectroscopy analysis. IgG samples were digested by trypsin. Briefly, IgG was reduced with Dithiothreitol for 30 min at 56° C. and alkylated with iodoacetamide for 30 min in the dark. Trypsin digestion was performed at 37° C. overnight. Peptides were desalted using C18 HyperSep Filer Plates, dried using SpeedVac and resuspended in 0.1% formic acid and 0.5% acetonitrile solution. Samples were kept at 10° C. and injected onto the chromatographic column. Samples were analyzed using a reveres-phase nano-liquid chromatography Ultiomate 3000 system connected to an Elite Orbitrap mass spectrometer. The MS was operated in positive mode and the survey MS scan in the range of m/z 300-2000 was obtained at a resolution of 60,000. MS/MS was performed using collision-induced dissociation (CID) and electron-transfer dissociation fragmentation (ETD). IgG Fc glycopeptide glycan compositions were identified and quantified by their characteristics retention times and accurate monoisotopic masses of doubly and triply charged ions of glycosylated tryptic peptide EDYNSTIR Crystallization, data collection, and structure determination Screening for crystallization conditions was performed using commercially available sparse-matrix screens in a sitting-drop vapor diffusion mode and nanodrop setup at 293 K. The crystals used for data collection were grown as follows: $E4_{Fab}$-CEPI and $E4_{Fab}$-CII-C-13—The sitting drop was pipetted from 1 µl protein solution (8 mg/ml in 20 mM Tris pH 7.4, 20 mM NaCl) and 0.5 µl reservoir solution (20% (w/v) PEG33S0, 0.1 M ammonium citrate pH S.0). $E4_{Fab}$-CII-C-48—The sitting drop was set up from 0.1 µl protein solution (10 mg/ml in 20 mM Tris pH 7.4, 20 mM NaCl) and 0.2 µl reservoir solution (15% (w/v) PEG 6000, 0.1 M Tris pH 8.S). $E4_{Fab}$—The sitting drop consisted of 0.1 µl of 10 mg/ml complex in 20 mM Tris pH7.4, S0 mM NaCl, and 0.2 µl of reservoir solution (20% (w/v) PEG 6000, 0.2 M ammonium chloride 0.1 M MES pH 7.0). $DI0_{Fab}$—The hanging drop was pipetted from 1 µl of 7 mg/ml $DI0_{Fab}$ mixed with CEPI in 2-fold molar excess and 50 mM NDSB-2S6 in 20 mM Tris pH 7.S, 20 mM NaCl and 0.5 µl reservoir solution (2.55 M ammonium sulfate, 0.1 M sodium citrate pH 4.7S).$B2_{Fab}$—The sitting drop consisted of 0.2 µl of 10 mg/ml $B2_{Fab}$-P6 (P6: HACitEIFDSCitG-NH2, truncated version of CEPI) in 20 mM Tris pH 7.4, 50 mM NaCl, and 0.1 µl of reservoir solution (20% PEG 33S0,0.2 M tri-sodium citrate).

Except for $DI0_{Fab}$, all crystals were cryoprotected by brief soaking in the corresponding reservoir solution containing 25% (v/v) ethylene glycol ($E4_{Fab}$-CII-013) or glycerol (all others) before flash-freezing in liquid nitrogen. Diffraction data were collected at the beamlines. The images were processed using XIA2, and scaled by AIMLESS from the CCP4 program suite.

The structure of $E4_{Fab}$-CII-C-13 was determined by molecular replacement using PHASER and as search models ensembles of five light chain models split into individual domains and five heavy chain models derived from antibodies most homologous in sequence (heavy chains of PDB entries: IORQ,4HCI, 4MIG, 3LEY, 1NCW; light chains of PDB-entries 3LMJ, 5ALC, 3D69, 4ODH). All other $E4_{Fab}$ structures were determined using the heavy and light chain constant domain and variable domain dimers of the solved $E4_{Fab}$-CII-C-13 structure as search models. The structures of $B2_{Fab}$ and $DI0_{Fab}$ were also solved by molecular replacement in PHASER. The crystal structure of the human FabI5 Mut8 (PDB accession code: 3NCJ) was used as search model for $B2_{Fab}$, whereas the structure of $DI0_{Fab}$ was determined with the light chain of the neutralizing antibody Fab fragment of PDB entry 4DAG, and the heavy chain of the Fab fragment of PDB entry 2ZUQ as search models.

Continuous and well-defined electron density was observed for the entire light chain and almost all heavy chain residues of the respective Fab fragments, as well as for parts of the three peptides cocrystallized with the $E4_{Fab}$. Iterative cycles of the manual model building using COOT and TLS and restrained refinement with Phenix or REFMACS were used until R-factors converged. About 5% of the reflections were randomly selected and set aside for unbiased cross-validation (calculation of $R_{free}$). All final models have good stereochemistry, with >96% of the residues in the most favored regions of the Ramachandran plot. The "Protein Interfaces, Surfaces and Assemblies" service PISA at the European Bioinformatics Institute (www.ebi.ac.uk/pdbe/prot_int/pistart.html) was used to analyze molecular surfaces, CONTACT of the CCP4 suite to analyse the peptide interactions, and Phenix for calculation of elbow angles. The structure comparisons and RMSD calculations were performed with SSM as implemented in COOT. The crystallographic coordinates and structure factors have been deposited in the Protein Data Bank with the accession codes listed in Table I.

Conclusion: The crystal structures of the ACPA E4 bound to citrullinated peptides revealed conserved interactions with the citrulline residue, but different patterns for how the neighboring amino acids in the peptides epitopes are recognized. The citrulline is deeply inserted into a narrow pocket of the $E4_{Fab}$ paratope where it is specifically recognized by the formation of three hydrogen bonds to its side chain. The rather nonpolar character of this pocket biases against recognition of corresponding unmodified epitopes. Almost all the hydrogen-bonding interactions between the remaining epitope residues and the antibody CDR loops of engage peptide main chain groups, allowing for extensive cross-reactivity.

Example 5: Autoantibodies Against E4-Bound Citrullinated Peptides in RA

To evaluate the prevalence of the E4-bound Cit-peptides in RA patients, we selected the three representative Cit-peptides that were co-crystallized with E4 as potential targets and measured their autoantibody levels in two large cohorts (EIRA, and TIRA2) by Luminex immunoassay.

Peptides CII-C-13-Cit (CPAGEEGKXGARGEPGCA, X=citrulline) (SEQ ID NO:20) and CII-C-48-Cit (CEAGEPGEXGLKGHRGCA) (SEQ ID NO:21) are derived from CII, whereas CEP1 (CKIHAXEIFDSXGNPTVECK) (SEQ ID NO:22) is a well-characterized peptide originating from enolase.

Figure 7A:
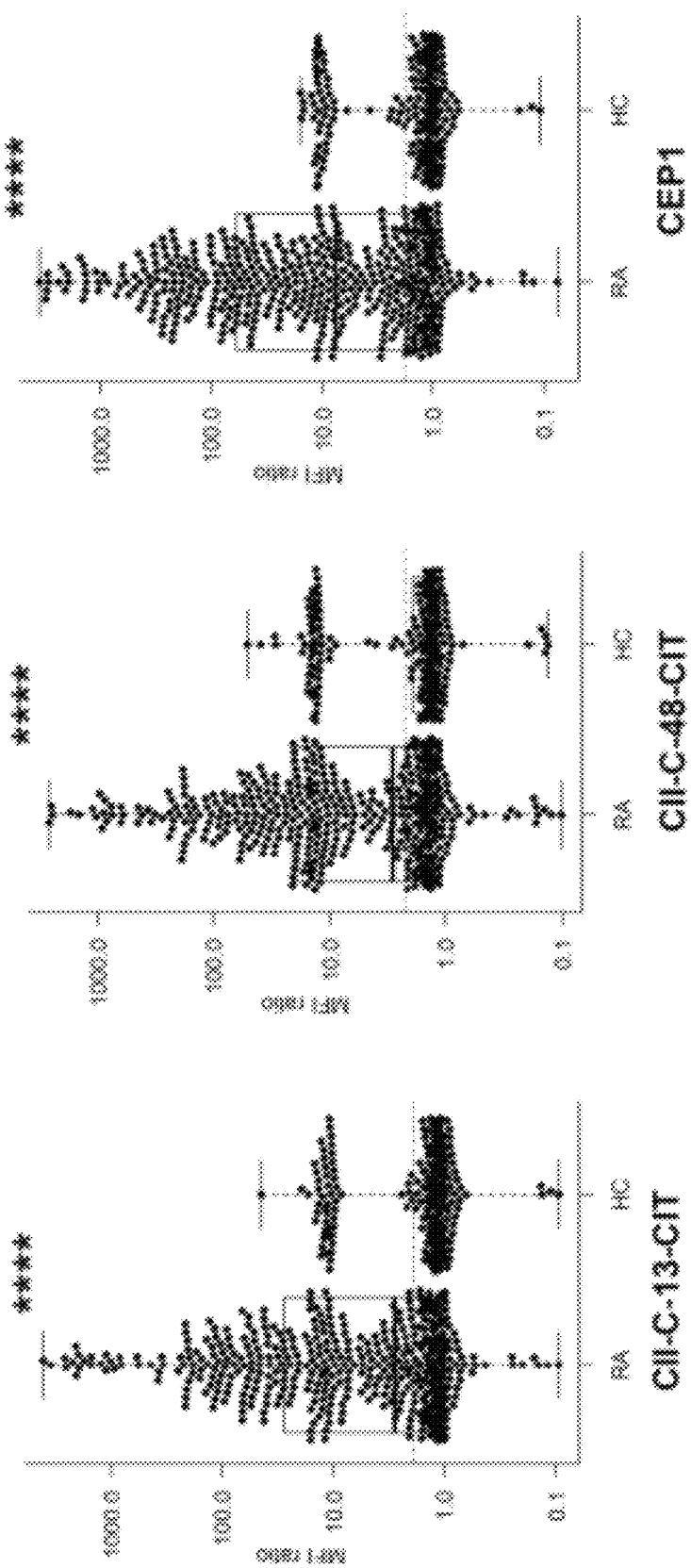
Figure 7B:
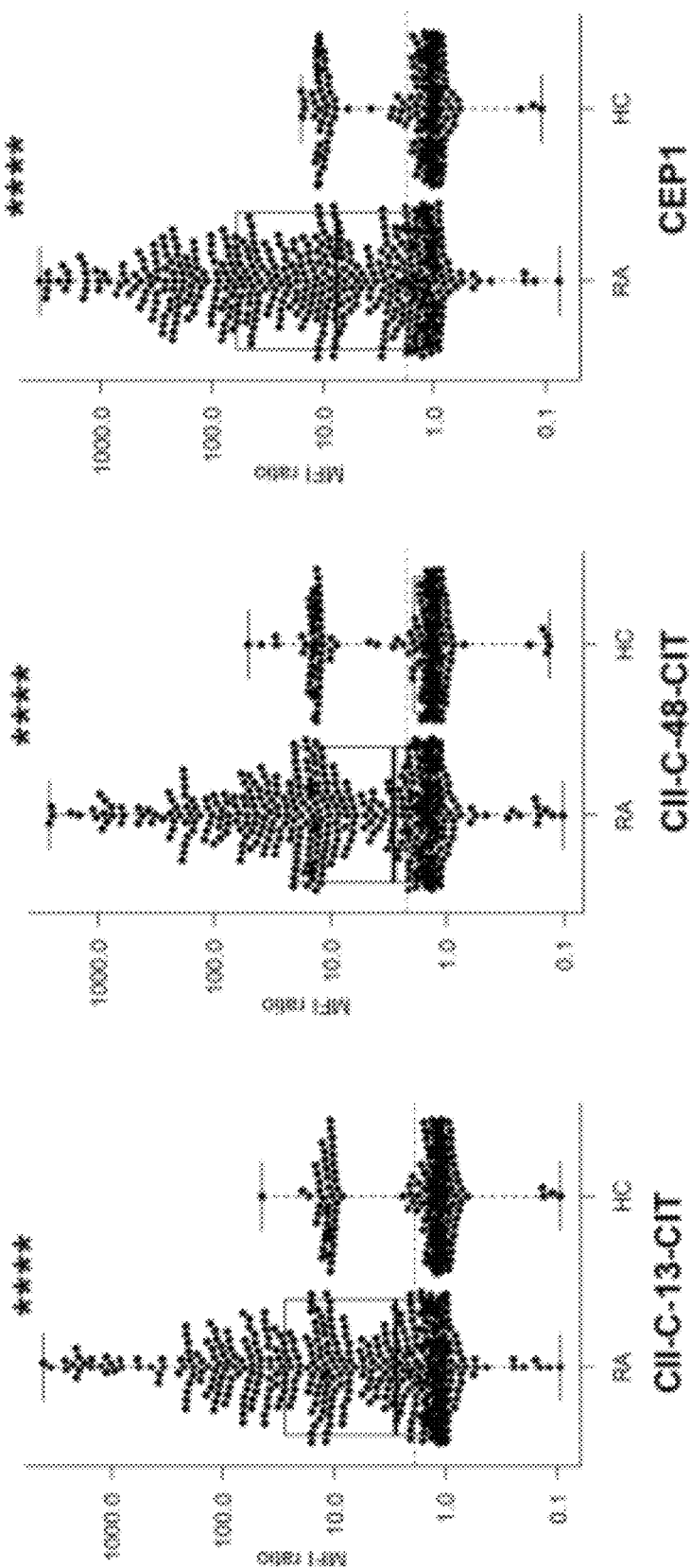
Figure 7C:
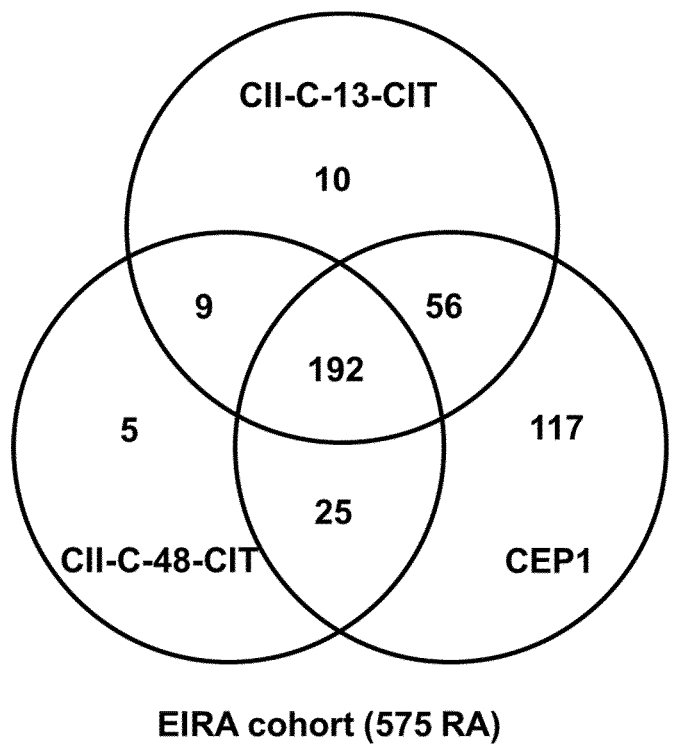
Figure 7C:
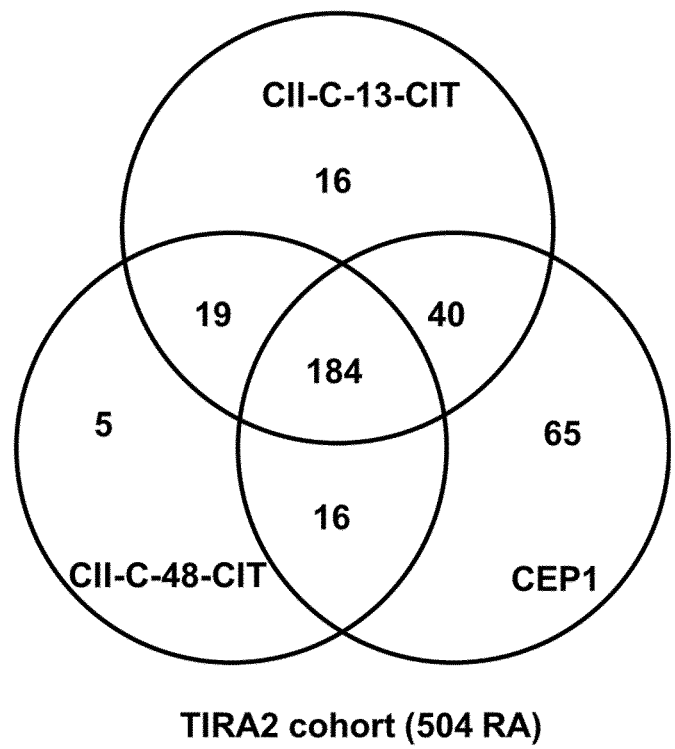

A statistically significant difference in antibody responses between healthy controls and RA patients was clearly seen in both two cohorts for CEP1, CII-C-13, and CII-C-48 (FIG. 7A-B, Table. 3). Approximately 46% of the RA patients in the EIRA cohort (51% in TIRA2) responded to the citrullinated CII-C-13, which is comparable to the reactivity towards citrullinated CII-C-48 (40% in EIRA, and 44% in TIRA2). The sensitivity for CEP1 was higher than that for the two citrullinated CII peptides in both cohorts (68% in EIRA, and 61% in TIRA2). In addition, about 40% of RA patients in both cohorts reacted against all three citrullinated peptides (FIG. 7C), suggesting that a significant proportion of antibodies in RA shows a high degree of cross-reactivity.

TABLE 3

Diagnostic performance of citrullinated peptides by Luminex immunoassay in EIRA (RA = 575 and Healthy control = 191) and TIRA2 cohort (RA = 504 and Healthy control = 285)

| Peptide | Sensitivity | | Specificity | |
|---|---|---|---|---|
| | EIRA | TIRA2 | EIRA | TIRA2 |
| CII-C-13-R | 1.2% | 8.5% | 99.5% | 93.7% |
| CII-C-13-CIT | 46.4% | 51.4% | 97.4% | 98.6% |
| CII-C-48-R | 1.6% | 0.6% | 98.4% | 98.9% |
| CII-C-48-CIT | 40.2% | 44.4% | 96.9% | 96.8% |
| REP1 | 8.0% | 8.3% | 98.4% | 91.9% |
| CEP1 | 67.8% | 60.5% | 96.3% | 96.5% |

The cutoff for calculation of sensitivity and specificity is based on (median + 5 × median absolute deviation) of the healthy control group.

Materials and Methods

Patient population. In the present study, samples from two cohorts of RA patients were used for the Luminex immunoassay. First, a part of the TIRA2 cohort (n=504) was used (Svard et al., 2015)Symptom duration was at least 6 weeks but no more than 12 months. At the time of serum sampling (i.e. baseline), none of the patients were being treated with disease-modifying antirheumatic drugs. Healthy subjects from the Western Region Initiative to Gather Information on Atherosclerosis (WINGA) cohort (n=284) served as controls for the TIRA-2 cohort. Second, a subset of the previously described EIRA cohort (Stolt et al., 2003), consisting of 575 RA patients and 191 healthy controls, were used. RA in EIRA was diagnosed according to the American College of Rheumatology (ACR) 1987 criteria (Arnett et al., 1988).

Suspension bead array. Autoantibody response was analyzed by the Luminex technology as described previously (Ayoglu et al., 2013). Briefly, all biotinylated peptides were captured on beads to which NeutrAvidin had been immobilized. Human serum samples were diluted in assay buffer (3% BSA, 5% milk powder, 0.1% ProClin300, 0,05% Tween 20, 100 µg/mL NeutrAvidin in phosphate buffered saline (PBS)) and incubated for 1 h at room temperature (RT) on a shaker. Then the serum samples were transferred to a 384-well plate containing peptide-coated beads by a liquid handler (CyBi-SELMA, CyBio). After incubation at RT on a shaker for 75 min, all beads were washed with Tween-20 in PBS (PBST) on a plate washer, and then re-suspended in a solution containing the secondary anti-human IgG Fcγ-PE. After 40 min incubation, the beads were washed with PBST and measured in a FlexMap3D. The median fluorescence intensity (MFI) was used to quantify the interaction of serum antibody with the given peptides. For the comparison of responses to the cyclic peptides in RA cohorts, the ratio value, calculated by dividing the raw value by the median value of 5 least responsive cyclic arginine-containing control peptides, was reported.

Conclusion: There is a difference in antibody responses between healthy controls and RA patients for CEP1, CII-C-13, and CII-C-48. In addition, a significant proportion of antibodies in RA shows a high degree of cross-reactivity.

REFERENCES

Amara, K. et al. Monoclonal IgG antibodies generated from joint-derived B cells of RA patients have a strong bias toward citrullinated autoantigen recognition, J Exp Med 210(3), 445-55, 2013

Arnett, F. C. et al. The American Rheumatism Association 1987 revised criteria for the classification of rheumatoid arthritis. Arthritis Rheum 31(3), 315-24, 1988

Ayoglu, B. et al. Autoantibody profiling in multiple sclerosis using arrays of human protein fragments. Mol Cell Proteomics 12(9), 2657-72, 2013

Burska, A. N. et al. Autoantibodies to Posttranslational Modifications in Rheumatoid Arthritis. Mediat Inflamm, 2014

Chirivi. R. G. S. et al. Anti-Citrullinated Protein Antibodies as Novel Therapeutic Drugs in Rheumatoid Arthritis. J Clin Cell Immunol, S6:006, 2013

Ge, C. et al. Anti-citrullinated protein antibodies cause arthritis by cross-reactivity to joint cartilage. JCI Insight 2, 2017

Ge, C et al. Structural basis of cross-reactivity of anti-citrullinated protein antibodies. Arthritis Rheumatol. 2018 Aug. 27

Haag, S. et al. Identification of New Citrulline-Specific Autoantibodies, Which Bind to Human Arthritic Cartilage, by Mass Spectrometric Analysis of Citrullinated Type II Collagen. Arthritis Rheumatol 66, 1440-1449, 2014

Harre, U. et al. Glycosylation of immunoglobulin G determines osteoclast differentiation and bone loss. Nat Commun 6, 6651, 2015

Harre, U. et al. Induction of osteoclastogenesis and bone loss by human autoantibodies against citrullinated vimentin. J Clin Invest 122, 1791-1802, 2012

Ioan-Facsinay, A. et al. Anti-cyclic citrullinated peptide antibodies are a collection of anti-citrullinated protein antibodies and contain overlapping and non-overlapping reactivities. Ann Rheum Dis 70, 188-193, 2011

Khmaladze, I. et al. Mannan induces ROS-regulated, IL-17A-dependent psoriasis arthritis-like disease in mice. Proc Natl Acad Sci USA 111(35), E3669-78, 2014

Krishnamuthy A et al. Identification of a novel chemokine-dependent molecular mechanism underlying rheumatoid arthritis-associated autoantibody-mediated bone loss. Ann Rheum Dis. 2016; 75(4):721-9

McInnes, I. B. & Schett, G. The pathogenesis of rheumatoid arthritis. N Engl J Med 365, 2205-2219, 2011

Raats J. M. et al. Recombinant human monoclonal autoantibodies specific for citrulline-containing peptides from phage display libraries derived from patients with rheumatoid arthritis. J Rheumatol 30, 1696-711, 2003

Rombouts, Y. et al. Extensive glycosylation of ACPA-IgG variable domains modulates binding to citrullinated antigens in rheumatoid arthritis. Ann Rheum Dis 75, 578-585, 2016

Rombouts, Y. et al. Anti-citrullinated protein antibodies acquire a pro-inflammatory Fc glycosylation phenotype prior to the onset of rheumatoid arthritis. Ann Rheum Dis 74, 234-241, 2015

Schauer, C. et al. Aggregated neutrophil extracellular traps limit inflammation by degrading cytokines and chemokines. Nat Med 20(5), 511-7, 2014

Steiner, G. & Smolen, J. Autoantibodies in rheumatoid arthritis and their clinical significance. Arthritis Res 4 Suppl 2, S1-5, 2002

Stolt, P. et al. Quantification of the influence of cigarette smoking on rheumatoid arthritis: results from a population based case-control study, using incident cases. Ann Rheum Dis 62(9), 835-41, 2003

Svard, A. et al. Associations with smoking and shared epitope differ between IgA- and IgG-class antibodies to cyclic citrullinated peptides in early rheumatoid arthritis. Arthritis Rheumatol 67(8), 2032-7, 2015

Trier, N. H. et al. Contribution of Peptide Backbone to Anti-Citrullinated Peptide Antibody Reactivity. PLoS One 10, e0144707, 2015

Trier, N. H., et al. Cross-reactivity of a human IgG(1) anticitrullinated fibrinogen monoclonal antibody to a citrullinated profilaggrin peptide. Protein Sci 21, 1929-1941, 2012

Trouw, L. A. et al. Anti-Cyclic Citrullinated Peptide Antibodies From Rheumatoid Arthritis Patients Activate Complement via Both the Classical and Alternative Pathways. Arthritis and Rheumatism 60, 1923-1931, 2009

Uysal, H. et al. Structure and pathogenicity of antibodies specific for citrullinated collagen type II in experimental arthritis. J Exp Med 206, 449-462, 2009 van de Stadt L A, et al. The extent of the anti-citrullinated protein antibody repertoire is associated with arthritis development in patients with seropositive arthralgia. Ann Rheum Dis 70, 128-33, 2011 van de Stadt, L. A. et al. Monoclonal anti-citrullinated protein antibodies selected on citrullinated fibrinogen have distinct targets with different cross-reactivity patterns. Rheumatology (Oxford) 52, 631-635, 2013 van Gaalen, F. A. et al. Autoantibodies to cyclic citrullinated peptides predict progression to rheumatoid arthritis in patients with undifferentiated arthritis: a prospective cohort study. Arthritis Rheum 50, 709-715, 2004

Waaler, E. On the occurrence of a factor in human serum activating the specific agglutination of sheep blood corpuscles. 1939. APMIS 115, 422-438, 2007

Wigerblad, G. et al. Autoantibodies to citrullinated proteins induce joint pain independent of inflammation via a chemokine-dependent mechanism. Ann Rheum Dis 75, 730-738, 2016

The invention claimed is:

1. An antibody or antibody fragment comprising a variable heavy chain (VH) domain and a variable light chain (VL) domain, and wherein
   (a) the VH domain comprises an amino acid sequence that includes complementarity determining regions (CDRs):
   a CDR1 sequence comprising an amino acid sequence as set forth in SEQ ID NO: 1;
   a CDR2 sequence comprising an amino acid sequence as set forth in SEQ ID NO: 3; and
   a CDR3 sequence comprising an amino acid sequence as set forth in SEQ ID NO: 4 and
   (b) the VL domain comprises an amino acid sequence that includes complementarity determining regions (CDRs):
   a CDR4 sequence comprising an amino acid sequence as set forth in SEQ ID NO: 5;
   a CDR5 sequence comprising an amino acid sequence as set forth in SEQ ID NO: 6; and
   a CDR6 sequence comprising an amino acid sequence as set forth in SEQ ID NO: 7.

2. The antibody or antibody fragment according to claim 1, wherein
   the VH domain comprises an amino acid sequence selected from the group consisting of SEQ ID NOs: 23 and 24; and
   the VL domain comprises an amino acid sequence selected from the group consisting of SEQ ID NOs: 12 and 14.

3. The antibody or antibody fragment according to claim 1, wherein
   the VH domain comprises an amino acid sequence having at least 90% sequence identity SEQ ID NO: 23, and the VL domain comprises an amino acid sequence having at least 90% sequence identity SEQ ID NO: 12.

4. The antibody or antibody fragment according to claim 3 wherein the VH domain comprises the sequence of SEQ ID NO: 23 or 24, linked to the CH region of SEQ ID NO: 16 and the VL domain comprises the sequence of SEQ ID NO: 12 or 14 linked to the CL region of SEQ ID NO:17.

5. The antibody or the antibody fragment according to claim 1, wherein the antibody or antibody fragment binds to a citrullinated peptide.

6. The antibody or the antibody fragment according to claim 1, wherein the antibody or antibody fragment comprise a VH domain and a VL domain each in a separate polypeptide sequence.

7. The antibody or the antibody fragment according to claim 1, wherein the VH domain is conjugated to a CH region.

8. A method for treatment of an autoimmune disease or disorder, the method comprising administering the antibody or the antibody fragment according to claim 1 to a subject in need thereof, wherein the autoimmune disease or disorder is rheumatoid arthritis.

9. The antibody or antibody fragment of claim 1, wherein the VH domain and the VL domain are grafted onto a protein scaffold of an immunoglobulin.

10. The antibody or antibody fragment of claim 9, wherein the immunoglobulin is an IgA, IgE, an IgG1, IgG2a, an IgG2b, an IgG3, or an IgM.

11. The antibody or antibody fragment thereof of claim 1, wherein the antibody or antibody fragment is recombinant.

12. The antibody or antibody fragment according to claim 1, wherein the VH domain comprises an amino acid sequence having at least 90% sequence identity SEQ ID NO: 23, and the VL domain comprises an amino acid sequence having at least 90% sequence identity SEQ ID NO: 14.

13. The antibody or antibody fragment according to claim 1, wherein the VH domain comprises an amino acid sequence having at least 90% sequence identity SEQ ID NO: 24, and the VL domain comprises an amino acid sequence having at least 90% sequence identity SEQ ID NO: 12.

14. The antibody or antibody fragment according to claim 1, wherein the VH domain comprises an amino acid sequence having at least 90% sequence identity SEQ ID NO: 24, and the VL domain comprises an amino acid sequence having at least 90% sequence identity SEQ ID NO: 14.

\* \* \* \* \*